US 6,197,007 B1

(12) United States Patent
Thorne et al.

(10) Patent No.: US 6,197,007 B1
(45) Date of Patent: Mar. 6, 2001

(54) IN-LINE RETRACTABLE SAFETY MEDICAL NEEDLE ASSEMBLY

(76) Inventors: David L. Thorne, 1759 S. 450 E., Kaysville, UT (US) 84037; Roy L. Barrus, 741 W. 2350 North, West Bountiful, UT (US) 84087; Kendall P. Thorne; Gale H. Thorne, both of 1056 Millcrest Cir., Bountiful, UT (US) 84010

( * ) Notice: Subject to any disclaimer, the term of this patent is extended or adjusted under 35 U.S.C. 154(b) by 0 days.

(21) Appl. No.: 09/221,720

(22) Filed: Feb. 4, 1999

(51) Int. Cl.⁷ ..................................... A61M 5/00
(52) U.S. Cl. ............... 604/263; 604/164.01; 604/165.03; 604/171
(58) Field of Search ............... 604/263, 164.01, 604/164.11, 165.03, 171, 523

(56) References Cited

U.S. PATENT DOCUMENTS

| 3,574,306 | 4/1971 | Alden | ................................ 128/214.4 |
| 4,676,783 | 6/1987 | Jagger | ............................... 604/213 |

(List continued on next page.)

FOREIGN PATENT DOCUMENTS

| 0 008 451 | 3/1980 | (EP) | ............................. A61M/25/00 |
| 0 033 207 | 8/1981 | (EP) | ............................. A61M/5/14 |
| 0 443 735 A1 | 8/1991 | (EP) | ............................. A61M/5/32 |
| 0 494 932 B1 | 7/1992 | (EP) | ............................. A61M/5/32 |
| 0 499 077 A1 | 8/1992 | (EP) | ............................. A61M/25/06 |
| 0 499 077 B1 | 8/1992 | (EP) | ............................. A61M/25/06 |
| 0 521 145 B1 | 1/1993 | (EP) | ............................. A61M/5/32 |
| 0 534 000 A2 | 3/1993 | (EP) | ............................. A61M/25/06 |
| 0 534 000 B1 | 3/1993 | (EP) | ............................. A61M/25/06 |
| 0 558 162 A2 | 9/1993 | (EP) | ............................. A61M/25/06 |
| 0 558 162 B1 | 9/1993 | (EP) | ............................. A61M/25/06 |
| 0 566 769 A1 | 10/1993 | (EP) | ............................. A61M/25/06 |
| 0 566 769 B1 | 10/1993 | (EP) | ............................. A61M/25/06 |
| 0 436 646 B1 | 8/1994 | (EP) | ............................. A61M/5/32 |
| 0 615 765 A1 | 9/1994 | (EP) | ............................. A61M/25/06 |
| 0 664 139 A1 | 7/1995 | (EP) | ............................. A61M/25/06 |
| 0 692 277 A2 | 1/1996 | (EP) | ............................. A61M/25/06 |
| 0 745 399 A1 | 12/1996 | (EP) | ............................. A61M/5/14 |
| 0 830 871 A2 | 3/1998 | (EP) | ............................. A61M/25/06 |

*Primary Examiner*—John D. Yasko
(74) *Attorney, Agent, or Firm*—Paul S. Evans; Gale H. Thorne

(57) ABSTRACT

Disclosure of methods and apparatus providing bases for design of compact small bore medical needle retraction safety devices wherein actuators are displaced away from slender needle sheathing bodies to initiate a needle retraction cycle for safely containing a medical needle after use. Such actuation guards against inadvertent acts, such as depression of an actuator, which may result in untimely needle retraction. Four embodiments of the instant invention are disclosed. In one embodiment, needle retracting energy is stored as a medical needle is extended for use and is expended to retract the needle into safe containment. Other embodiments comprise power assist mechanisms which store energy during an initial phase of needle retraction to be used to enhance and assist needle retraction during a needle retraction completing phase. In some embodiments, retraction is facilitated by a pair of rigid, elongated, hingedly interconnected arms which are further hingedly coupled to a needle hub assembly and to a device body such that one arm is rotated approximately 180° to retract the needle a distance greater than the length of the so rotated arm to facilitate retraction actuation. One power assist mechanism comprises a part molded as a distortable member of one of the arms. To realize low cost manufacture, the operating device can be made from as few as two injection molded parts. A readily viewable, blood flash chamber permits early detection of needle entry into a blood vessel.

23 Claims, 26 Drawing Sheets

U.S. PATENT DOCUMENTS

| | | | |
|---|---|---|---|
| 4,762,516 | 8/1988 | Luther | 604/164 |
| 4,832,696 | 5/1989 | Luther | 604/164 |
| 4,966,591 | 10/1990 | Yuen | 604/192 |
| 5,030,212 | 7/1991 | Rose | 604/263 |
| 5,085,639 | 2/1992 | Ryan | 604/110 |
| 5,088,982 | 2/1992 | Ryan | 604/110 |
| 5,108,376 | 4/1992 | Bonaldo | 604/171 |
| 5,112,311 | 5/1992 | Utterberg | 604/177 |
| 5,120,311 | 6/1992 | Sagstetter | 604/110 |
| 5,120,320 | 6/1992 | Fayngold | 604/177 |
| 5,154,699 | 10/1992 | Ryan | 604/116 |
| 5,176,655 | 1/1993 | Mccormick | 604/198 |
| 5,188,611 | 2/1993 | Orgain | 604/192 |
| 5,219,339 | 6/1993 | Saito | 604/198 |
| 5,266,072 | 11/1993 | Utterberg | 604/177 |
| 5,279,588 | 1/1994 | Nicoletti | 604/250 |
| 5,330,438 | 7/1994 | Gollobin | 604/177 |
| 5,350,368 | 9/1994 | Shields | 604/263 |
| 5,354,281 | 10/1994 | Chen | 604/177 |
| 5,385,554 | 1/1995 | Brimhall | 604/168 |
| 5,409,461 | 4/1995 | Steinman | 604/110 |
| 5,433,703 | 7/1995 | Utterberg | 604/52 |
| 5,447,501 | 9/1995 | Karlason | 604/198 |
| 5,498,241 | 3/1996 | Fabozzi | 604/177 |
| 5,501,672 | 3/1996 | Firth | 604/177 |
| 5,501,675 | 3/1996 | Erskine | 604/263 |
| 5,505,711 | 4/1996 | Arakawa | 604/171 |
| 5,520,654 | 5/1996 | Wahlberg | 604/164 |
| 5,549,571 | 8/1996 | Sak | 604/198 |
| 5,562,636 | 10/1996 | Utterberg | 604/263 |
| 5,562,637 | 10/1996 | Utterberg | 604/263 |
| 5,573,510 | 11/1996 | Isaacson | 604/158 |
| 5,690,619 | 11/1997 | Erskine | 604/263 |
| 5,704,924 | 1/1998 | Utterberg | 604/263 |
| 5,772,638 | 6/1998 | Utterberg | 604/263 |
| 5,779,679 | 7/1998 | Shaw | 604/158 |
| 5,795,339 | 8/1998 | Erskine | 604/264 |
| 5,830,190 | 11/1998 | Howell | 604/168 |
| 6,050,976 * | 4/2000 | Thorne et al. | 604/164 |

* cited by examiner

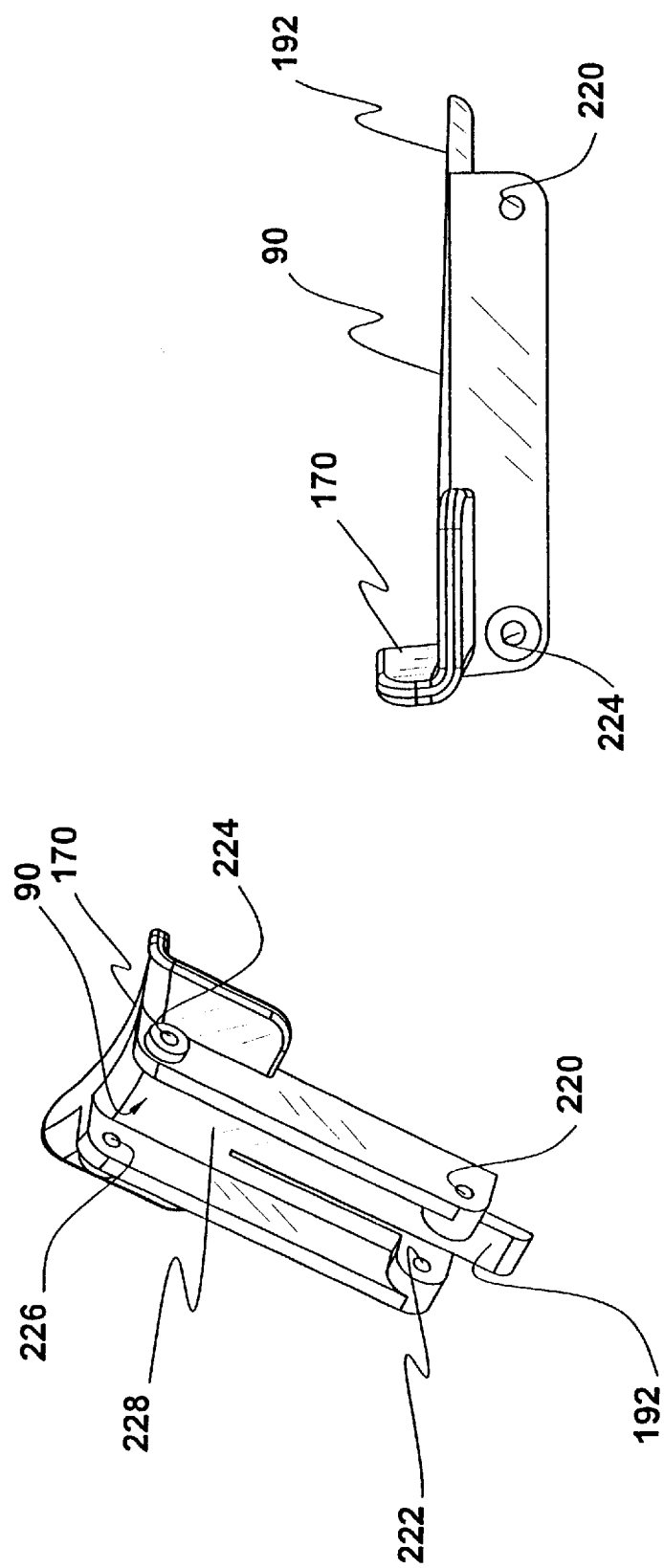

IN-LINE RETRACTABLE SAFETY MEDICAL NEEDLE ASSEMBLY

FIELD OF THE INVENTION

The present invention relates to safety products which generally pertain to hollow bore needle devices used in percutaneous medical procedures. Such products are aptly applied to conventional blood collection and other devices wherein a very small bore needle is shielded or otherwise secured, after being contaminated by use in the medical procedure, to minimize hazards of inadvertent injury and subsequent infection. Preferably, for further protection from contamination, the devices are limited to single-use and are disposable.

DESCRIPTION OF RELATED ART

Recognition of all too common occurrences of sickness which sometimes prove fatal due to diseases transmitted by inadvertent needle sticks has resulted in development of a wide variety of safety medical needle devices which are used in the areas of I.V. catheters, phlebotomy and syringe devices. Likely, due to the special size, market cost sensitivity and nature of specialized uses for small gauge needles and associated devices used in winged needle sets, the breadth of commercially available safety winged needle devices is more limited than for larger size needle devices. Examples of patents which protect currently commercially available winged needle safety devices are found in U.S. Pat. No. 5,174,655 issued Jan. 5, 1993 to McCormick et al. (McCormick '655) and in U.S. Pat. 5,120,320 issued Jan. 9, 1992 to Fayngold (Fayngold '320).

McCormick '655 discloses a disposable medical needle assembly comprising a guide which shields a needle withdrawn therein after use and limiting members which limit extraction of the needle from the guide as the needle is withdrawn into the guide. Further, a releasable abutment is disclosed in a winged version of a device which restricts movement of the needle during an insertion process. A spring biased blocking plate is taught to provide a restriction against distal extension of the needle from the guide after retraction and shielding. In another embodiment, a device having reduced wing size is disclosed wherein a proximally disposed manipulating member abuts but only restricts relative distal movement of the needle. Similar extraction limiting members are used in this version to restrict extraction of the needle from a shielding guide when the needle is retracted to a safety position.

Fayngold '320 discloses an intravenous infusion and/or blood collection assembly which incorporates a two-part shield which, when placed in cooperating relationship, allows accommodation of a conventional, unmodified blood collection needle and body, including wings associated with the blood collection needle and body. The wings are an inherent part of a needle retraction and locking mechanism for the assembly.

Generally, winged needle and small cannula size safety devices depend upon a stable first needle position where the needle is disposed for use and a second stable second needle position, within which the needle is safely disposed within the cover of a shield. In some cases, as in one embodiment of Fayngold '320, the stable first position is dependent upon formation of a needle movement restricting abutment provided by interaction between a needle hub and a portion of one or more wings, the one or more wings being required to be disposed in a predetermined position while the needle is extended to be used. In other cases, exemplified by McCormick '655, an interaction with one or more wings is integral to needle retraction into shielded state. It should be noted that, in some medical procedures (e.g. where angular articulation of a needle is necessary to facilely find entrance into a vessel), one or more wings on a device may be detrimental to successful accomplishment of a procedure. In such cases, inherent need for the one or more wings is counterproductive.

As it is generally considered prudent to leave one hand free to care for a patient, particularly to a wound site, from which a needle is being withdrawn, a natural consequence is a need for devices which are operable by a single hand. For this reason, devices which can be operated by a single hand or digit thereof are most often preferred over devices requiring more. Further, ease of manipulating the needle from the first position to the second position is an important characteristic of a safety device, requiring critical attention in conception and design. However, even though manipulation should be easy, needle retraction (when moving the needle from the first position to the second position) must not be inadvertent, especially when considering that use of such a needle may involve relatively long periods of time when the patient and needle insertion device are left unattended. As a consequence, a better device would more than likely be one which requires a deliberate action to change a state of a retraction mechanism from one stable state to another when the needle is retracted.

BRIEF SUMMARY AND OBJECTS OF THE INVENTION

In brief summary, this novel invention alleviates all of the known problems related to facile, single handed operation of winged and small cannula, safety hollow bore needle devices. The inventive concepts and processes inherent in the instant invention are basic to devices which comprise elongated, slender core structure for ease in maneuvering of the device to accomplish ready needle entry into difficult to access vessels, which retract needles into safe confines in line with long needle axes, which may have power assisted or powered retraction impelled by memory elements in which energy is stored during an initiation phase of needle retraction or is stored during needle extension in preparation for use in a particular medical procedure and which permit responsive, early visualization of a "blood flash" as the needle penetrates a blood vessel. For device cost containment and facile manufacture, all such inventive features may be incorporated through utilization of a single injection molded medical needle hub and another single injection molded body part. The body part acts as a handle used for facile percutaneous needle insertion and holds the hub in slideable confinement. Needle retraction actuation mechanisms are an inherent part of the body. The hub and associated needle may be proximally connected in communicating relationship with tubing and other items which are common to small cannula and winged needle apparatus.

Devices, which stem from the instant invention, may have or not have wings, as wings are not inherently required for function of the invention. Generally, such devices comprise a small diameter, hollow bore medical needle securely affixed in a needle hub. Preferably, for early determination of access to a blood vessel (seen as a flash of red), a flash chamber is provided as part of the needle hub and is closely disposed to the proximal end of the medical needle. Contents of the flash chamber are transmitted, to be seen by a practicing clinician, through a translucent portion of a surrounding elongated part of the body in which the hub resides. The flash chamber is so disposed to provide an early visualization of blood as near a needle puncture site as possible.

In all embodiments of the invention, the hub is slidably disposed, but securely contained within the elongated body. In unpowered and power assisted embodiments, the hub is securely, but hingeably affixed to an extendable member of the body which is further affixed to a needle retraction actuator. In powered retraction embodiments, the hub communicates with constraining body parts through a latch/catch mechanism and an energy storing component. In the various embodiments, devices may comprise unpowered needle retraction having all phases of needle retraction being the result of manual action against an actuator. Otherwise, devices may comprise power assisted retraction wherein approximately a latter half of needle retraction is compelled by energy stored in a part which is stressed during an initial portion of the actuation. In other embodiments, devices may comprise powered retraction resulting from energy stored in a part which is stressed by extension of the devices needle in an extendable/retractable needle embodiment of the present invention.

To guard against inadvertent needle retraction, actuation is induced by extending the actuator away from the rest of the body and needle hub rather than by depression of a release mechanism or in-line displacement. In all embodiments, the bodies and retraction mechanisms are of slender construction, according facile rotation about the long axis of the needle to aid in angulated needle penetration of difficult to access blood vessels.

In all embodiments, the body comprises an elongated cylindrical distal section having a distal orifice from which the needle extends for use in a medical procedure. A distal portion of the hub may also extend outward from the distal body orifice when the needle is disposed for use. Proximal from the distal orifice, the distal section acts as a shield for the distal, sharpened end of the needle when retracted for safety therein.

In manual retraction and power assisted embodiments, the body part comprises a pair of substantially rigid arms articulated to pivot relative to one another. In one of such embodiments, one of the rigid arms is superiorly disposed relative to the other arm and comprises a distal tab which is used as an actuator. The inter-arm hinge is disposed at distal ends of both arms when the needle is extended for use in a medical procedure. In the needle extended state, the inferiorly disposed rigid arm is also hingeably affixed at its proximal end to a medial site of a base portion of the body. In this state, the superiorly disposed arm is hinged at a proximal end to a proximal portion of the needle hub, thereby permitting the entire body part to be folded into a compact, low silhouette apparatus for easy handling.

To retract the needle into a protective shield afforded by the cylindrical distal section of the body, the distal tab is outwardly and proximally displaced, causing the inferiorly disposed arm to pivot about an angle of substantially 180°, thereby displacing the needle and hub in line with the long axis of the needle substantially twice the distance of the length of the inferiorly disposed arm. During needle retraction, the superiorly disposed arm is angulated away from the rest of the body until the inferiorly disposed arm is orthogonally disposed relative the body base and then, in a continuing proximally directed motion, reseated against the rest of the body parts as the needle is fully retracted.

For power assist, the superiorly disposed arm comprises a flexible, proximally extending part which is stressed against a portion of the needle hub as the superiorly disposed arm is outwardly displaced. Once the inferiorly disposed arm passes the point of orthogonality to form an acute angle with the body base, energy stored in the extending part urges the superiorly disposed arm inward toward the needle hub and, through the hinged connection, the inferiorly disposed arm to a state of lowest potential energy whereat the inferiorly disposed arm completes a displacement of approximately 180°. In the lowest potential energy state, the needle is fully retracted.

Thus, needle retraction is accomplished by a compact, in-line assembly whereby an actuator tab is rotated outward and proximally from the device body base to retract the needle hub and associated medical needle proximally until the needle is safely disposed within the distal segment. The action of retraction displaces the device between its two states of highest stability. The retraction action may be power assisted for facile operation.

Note that force applied along the long axis of the needle is least effective in displacing the needle when the needle is in the fully extended state and in the fully retracted state due to sine laws which apply to such application of force toward hinged parts. Thus, the most stable states of the device occur when the needle is fully extended and when the needle is fully retracted. Even so, to assure device stability a releasable catch may be provided when the needle is extended for use and a secure catch may be provided to assure needle capture upon retraction.

For facile use, the body may comprise a pair of handles, preferably laterally disposed relative to the retraction mechanism. Further, one or more wings may be affixed to the body, preferably in the region of the distal section as contemporary medical procedures associated with such devices may prefer such flexible wings.

In another embodiment, one of the rigid arms is also superiorly disposed relative to the other arm when the needle is extended for use. However in this embodiment, the superior/inferior relationship reverses as the needle is retracted.

In the state where the needle is disposed for use, the initially inferiorly disposed arm comprises a tab on its proximal end, the tab being used as a needle retraction actuator. To establish needle retracting linkages, a hingeable connection is made between the distal end of the initially inferiorly disposed arm and a proximal part of the needle hub. An inter-arm hinge is disposed proximally relative to the hub connection. The initially superiorly disposed arm comprises a distally disposed hinged connection to a base portion of the body.

In this embodiment, the tab and initially inferiorly disposed arm are pivoted outward from the rest of the body and distally to retract the needle. This arm pivots about an angle of approximately 180° whereupon it is displaced to be in superior relation relative to the other arm when the needle is retracted into the distal segment of the body.

The retraction may be assisted by an elastic member affixed between the initially superiorly disposed arm and the body because this arm is neither displaced nor rotated greater than 90° during needle retraction. As was the case in the earlier disclosed embodiment, energy is stored in the elastic member during an initial phase of needle retraction phase. That energy is released once the angle between the portion of the body distal to the inter-arm hinge and the most superior portion of the tabbed arm becomes acute. This energy release provides a powered assist to fully secure the needle inside the distal segment of the body. Once the initially inferiorly disposed arm passes the point of orthogonality, energy stored in the extension urges the superiorly disposed arm and, through the hinged connection, the inferiorly disposed arm to a state of lowest potential energy. In the lowest potential energy state, the needle is fully retracted.

Note, in this embodiment as well, that force applied in line with the long axis of the needle is least effective in displacing the needle when the needle is in the fully extended state and in the fully retracted state due to sine laws which apply to such application of force toward hinged parts. Thus, the most stable states of the device occur when the needle is fully extended and when the needle is fully retracted. Even so, to assure device stability a releasible catch may be provided when the needle is extended for use and a secure catch may be provided to assure needle capture upon retraction.

For facile use, the body of this embodiment may also comprise a pair of handles, preferably laterally disposed relative to the direction of retraction of the needle securing mechanism. Further, a one or more wings may be affixed to the body, preferably in the region of the distal section as contemporary medical procedures associated with such devices may prefer use of flexible wings for facile needle handling and percutaneous insertion.

Thus, needle retraction is accomplished by a compact, in-line assembly whereby an actuator tab is rotated outward and distally relative to the rest of a body of a needle safety device to retract a needle hub and associated medical needle proximally until the needle is safely disposed within a distal shielding segment of the body. The action of retraction displaces moving parts of the device between its two states of highest stability. The retraction action may be power assisted for facile operation.

The invention may also be applied to a fully powered device wherein a medical needle is extended from enclosed containment for use in a medical procedure and retracted by force of energy stored during needle extension. In its manufactured and transport state, the device comprises a needle protecting cover, a body and a needle hub and associated needle. The body and needle hub cooperate to provide a stable platform comprising a latch and catch to maintain a needle extended state. The body further comprises a needle retraction release actuator which is displaced proximally and outwardly from the rest of the body to release the latch from the catch to compel the needle and its sharpened tip to be retracted into the distal segment of the body.

Accordingly, it is a primary object to provide an easy-to-use, low-cost, low-silhouette winged needle device which, for safety, provides facile retraction of a used medical needle into a housing or shield to protect against inadvertent needle sticks from a contaminated needle.

It is an important object to provide such a safety winged needle device which may be formed using but two injection molded parts.

It is a very important object to provide a needle retraction actuation mechanism which responds only to a deliberate action to guard against inadvertent and unplanned needle retraction.

It is an object to provide a safety medical needle retraction device having states of highest stability when the needle is extended for use and when the needle is retracted for safety.

It is an object to provide a safety medical needle retraction device which is compact in a vertical direction while the device is used in a medical procedure.

It is an object to provide a safety medical needle retraction device which is compact in a direction transverse to the long axis of the needle to permit axial rotation about the long axis of the needle for facile access to difficult to enter blood vessels.

It is an object to provide a safety medical needle retraction device which affords visualization of a blood flash at the proximal end of the needle for an early indication of needle entry into a blood vessel.

It is a chief object to provide a safety medical needle retraction device wherein an actuator, which retracts the needle, operates substantially in line with the long axis of the needle.

It is a primary object to provide a power assisting safety needle retracting apparatus by which retraction is enhanced by action of energy stored during an initiation of a retraction cycle and released toward the end of the retraction cycle to complement completion of the needle retraction cycle.

It is also a primary object to provide a powered needle retraction apparatus by which retraction is powered by energy stored while the needle is extended for use.

It is an object to provide a safety medical needle device comprising retraction powering parts which are maintained in an unstressed state prior to a needle being extend for use, which store energy for retraction as the needle is extended for use and which release the energy to retract the needle only upon deliberate displacement of an actuator.

It is an object to provide a safety medical needle device having retraction power assisting parts which are maintained in an unstressed state during manufacture and storage and which are stressed to store energy during an early phase of needle retraction actuation and are disposed to release that energy to assist needle motion during a final phase of needle retraction.

These and other objects and features of the present invention will be apparent from the detailed description taken with reference to accompanying drawings.

BRIEF DESCRIPTION OF THE DRAWINGS

FIG. 9 is a perspective of a second articulating member of a device which is similar to a second articulating member of the device embodiment seen in FIG. 1, the differences being clearly enumerated hereafter.

FIG. 9A is a side elevation of the second articulating member seen in FIG. 9.

DETAILED DESCRIPTION OF THE ILLUSTRATED EMBODIMENTS

Unless otherwise specified in this description, the term proximal is used to indicate that segment of a device relatively close to a user of the device. The term distal refers to the segments which are relatively far from the user. Reference is now made to the embodiments illustrated in FIGS. 1–27 wherein like numerals are used to designate like parts throughout. In those cases where a second part performs a function similar to that of a first part, but is different in structure relative to the first part, a prime of the number assigned to the first part may be used. Reference is now made to FIGS. 1–12, which apply to one embodiment of the invention.

Figure 1:
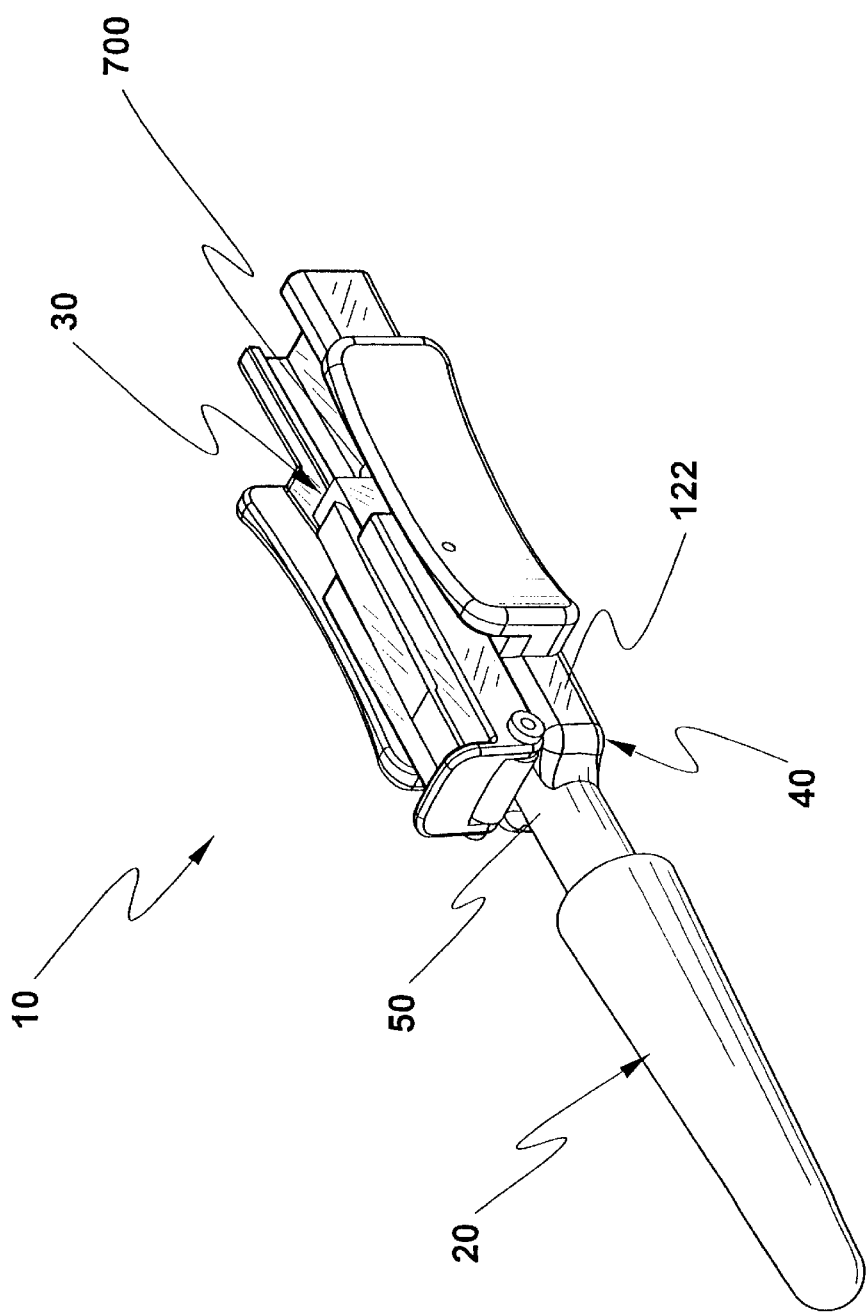
FIG. 1 is a perspective of an embodiment of the invention wherein a medical needle is disposed within a protective cap.

As seen in FIG. 1, this embodiment, generally referenced as device 10, comprises a needle cap 20, a needle hub assembly 30 and a body assembly 40. Device 10 may be provided in a package, such as a "bubble pack" to assure sterility at time of use, but is not shown as such packaging is common in contemporary medical device distribution. Body assembly 40 comprises an elongated, cylindrical distal segment 50 to which needle cap 20 is releasibly affixed.

Figure 2:
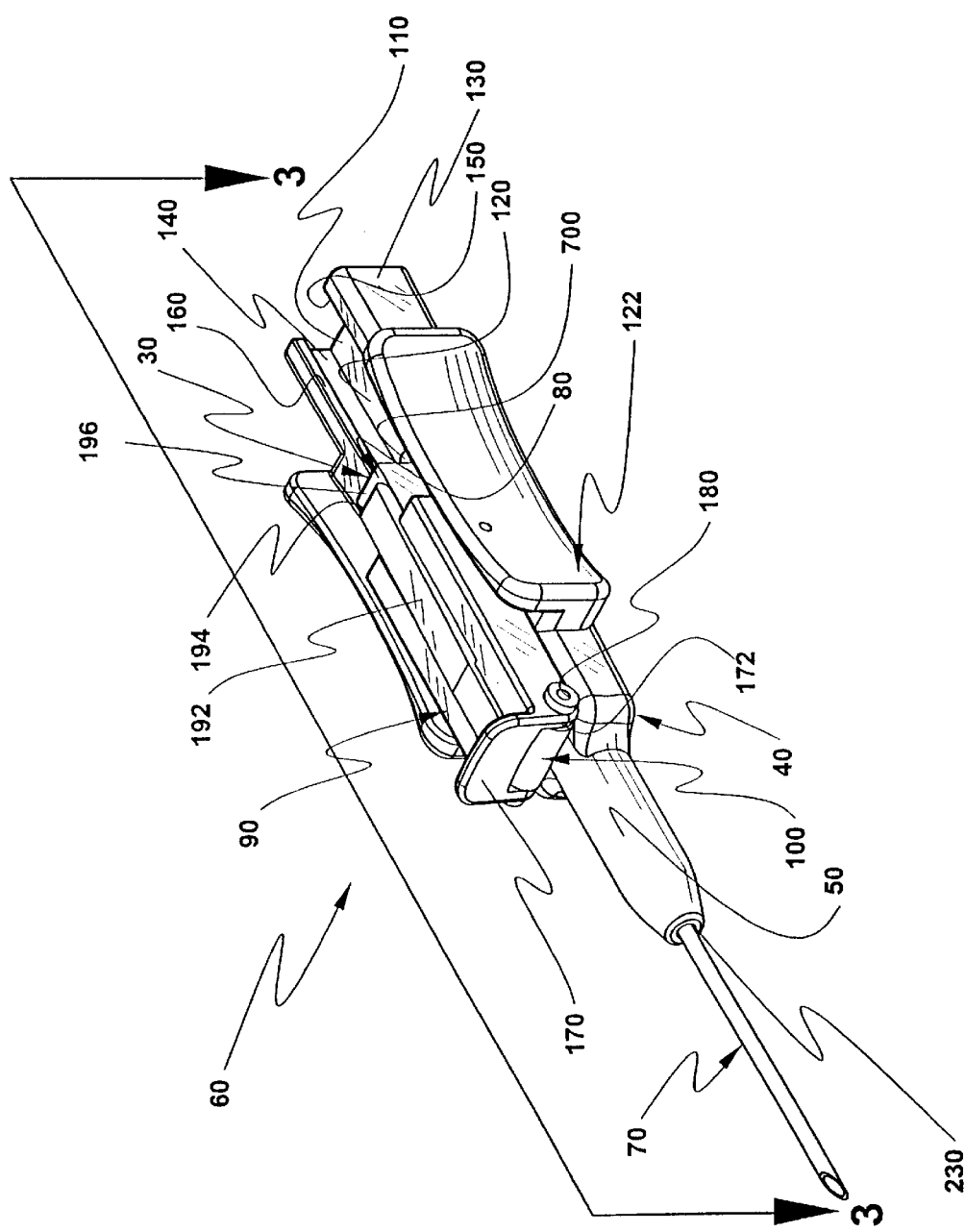
FIG. 2 is a perspective of the embodiment seen in FIG. 1 with the cap removed.

Device 10, with needle cap 20 removed, is referenced as device 60 in FIG. 2. In FIG. 2, device 60 is seen to further comprise a hollow bore medical needle 70 which is a part of needle hub assembly 30 and is securely affixed in a needle hub 80.

Body assembly 40 comprises a superiorly disposed arm 90, an inferiorly disposed arm 100 and a body base part 122. Body base part 122 comprises an elongated planar base section 120, which is contiguous with two opposing sides 130 and 140 which are essentially orthogonal to base section 120. Side 130 comprises an inwardly extending lip 150. In similar fashion, side 140 comprises an inwardly extending lip 160. In combination base section 120 and sides 130 and 140 with lips 150 and 160, respectively, combine to form a "U" shaped channel 110. So formed, "U" shaped channel 110 securely maintains hub assembly 30 in slidable containment as needle 70 is retracted from an extended state for use in a medical procedure to a retracted state where needle is enclosed for safety within distal segment 50.

Arm 90 comprises an actuator tab 170 and is affixed at distal end 172 to arm 100 by a hinge 180. As is better seen in FIG. 3, two other hinges which affix arm 90 to hub assembly 30 and arm 100 to body base part 122 are hinges 182 and 184, respectively. Note that base section 120 may be thickened proximally to permit needle 70 to facilely angulate toward a percutaneous entry site when resting upon a patient's skin surface.

Needle 70 may be securely affixed in needle hub 80 by adhesive, as is well known in contemporary medical device manufacture. Note that, between a proximal end 186 of needle 70 and actuator tab 170, there is a space where a blood flash may be viewed in a region indicated by number 188. For this reason, material used in body base part 122 and hub assembly 30 must be sufficiently translucent for the blood path to be clearly seen.

Figure 3:
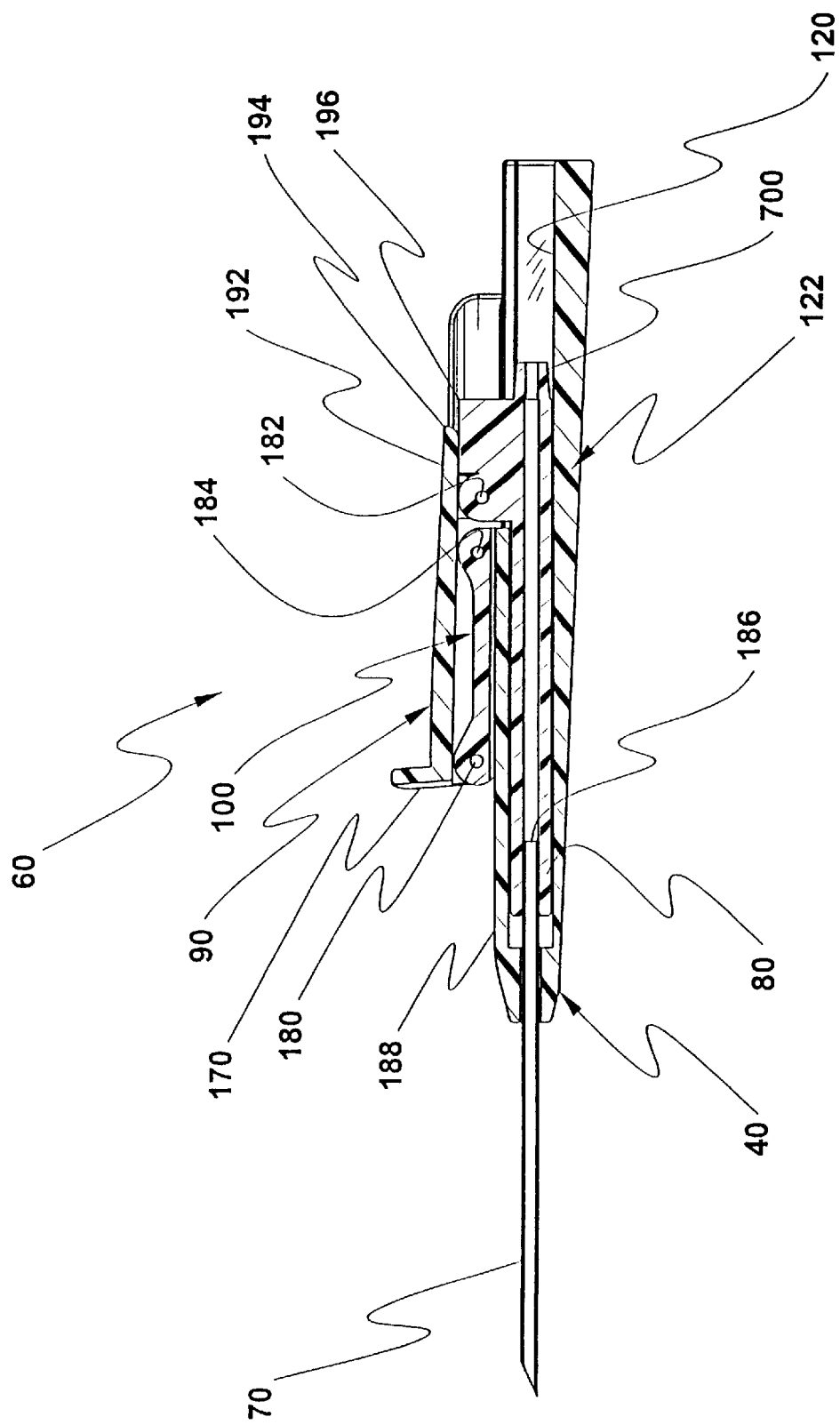
FIG. 3 is a side elevation cross section along lines 3—3 seen in FIG. 2.
Figure 4:
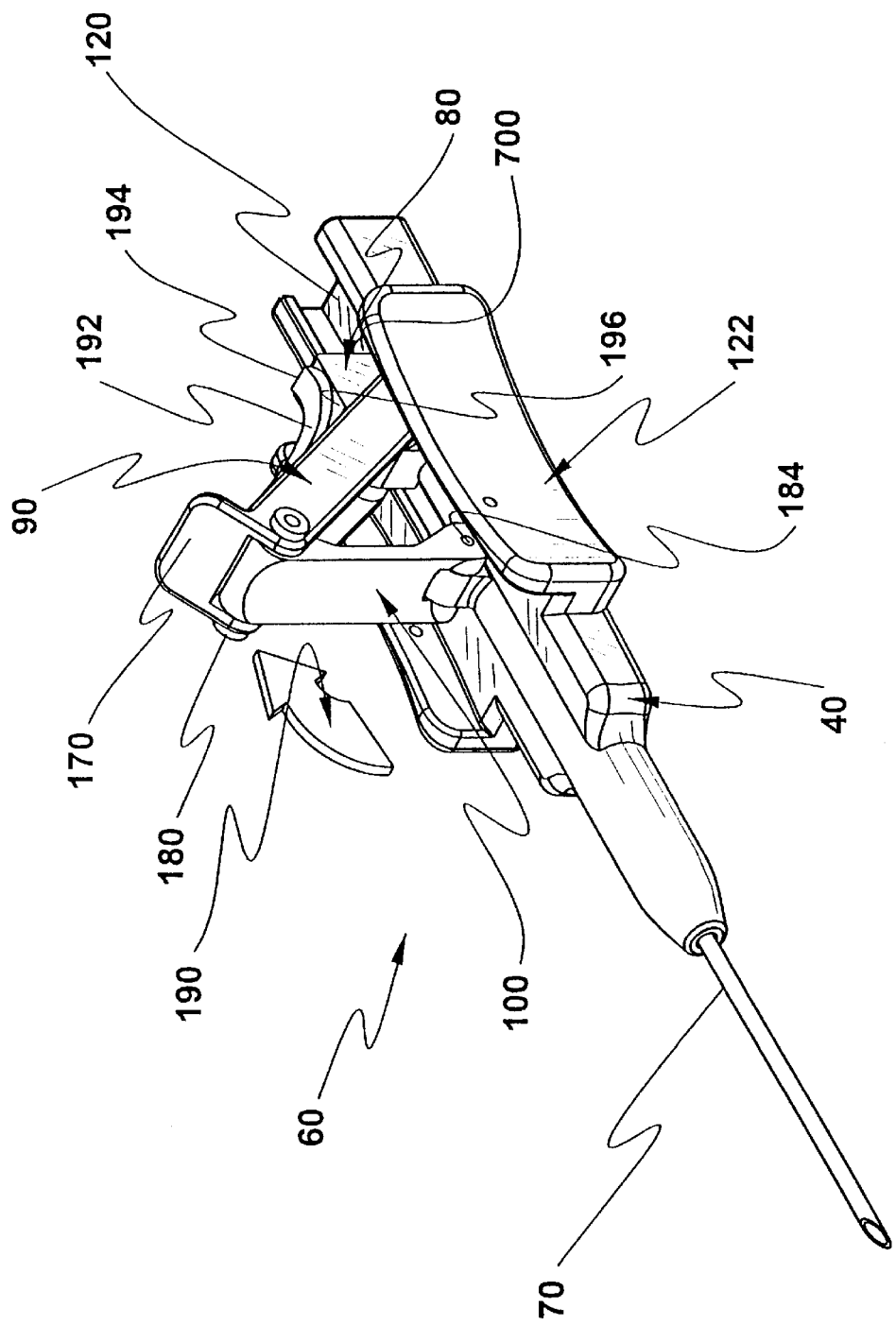
FIG. 4 is a perspective of the embodiment seen in FIGS. 1, 2 and 3, but having the needle displaced and partially retracted.

An intermediate state of device 60 in which needle 70 is being retracted is seen in FIG. 4. Application of force to tab 170 and arm 90, generally in the direction of arrow 190, causes arm 90 to pivot about hinge 182 (see FIG. 3) displacing tab 170 and arm 90 outwardly from the rest of body assembly 40. Note that force directed along the long axis of needle 70 or force directed inwardly toward body base part 122 will not effect needle 70 retraction. Through action at hinges 180 and 184, arm 100 is pivoted in a clockwise manner. Further, arm 90 comprises a reluctantly flexible elongated, medially disposed shaft 192 which is generally in a relaxed state as seen in FIGS. 2 and 3.

A proximal end 194 juxtaposes a top planar surface 196 of needle hub 80. Displacing arm 90, as seen in FIG. 4, causes shaft 192 to be elastically distorted thereby storing energy therein. The stored energy is directed toward returning arm 90 to a substantially parallel disposition relative to its original state. For this reason, when arm 100 passes through an orthogonal relationship to make an acute angle between with base section 120, the energy stored in shaft 192 forces arm 90 inwardly relative to base section 120 and, as a result, assists retraction of needle 70. In this manner, with appropriate spring tension physically attributed to shaft 192, articulating arm 100 just past the point of orthogonality relative to base section 120 permits completion of needle retraction without application of additional force.

It may be preferred to have the spring tension in shaft 192 produce a predetermined force during the completion of needle retraction. As an example, if it is desired to have a relatively constant return force applied through shaft 192 during the completion of needle retraction, a predetermined contour of surface 196 may be used to accomplish a controlled displacement of shaft 192 in the generation of the return force. If shaft 192 is designed such that the spring force in shaft 192, resulting from angular displacement of shaft 192 from the rest of arm 90 (α), is proportional to the angular displacement of arm 90 from base section 120 (Θ), then, α=k * Θ, where k is a spring constant which is dependent upon material and design characteristics of arm 90 and its shaft 192. Further, defining the length of shaft 192 from its free end to a point of connection with the rest of arm 90 is denoted by "⌊" and the length of a portion of arm 90 from hinge 182 to the point of connection of shaft 192 is denoted by "r", permits a geometric relationship to be established between a rotating arm 90 and shaft 192, as shaft 192 is constrained by contact with surface 196. Note that departure of surface 196 from a plane to one of variable contour causes a related variable force to be imposed upon shaft 192 and therefore upon arm 90 as shaft 192 is displaced along surface 196. So considered, formulae which describe the contour of surface 196 are:

$$y = r \sin \Theta - \lfloor \sin (1-k)\Theta$$

$$x = \lfloor \cos (1-k)\Theta - r \cos \Theta$$

where:
  y is a vertical distance measured from the surface of initial or at rest contact between shaft 192 and surface 196 and
  X is a distance, parallel to the top of base section 120, from hinge 182 to the contact point between shaft 192 and surface 196.

Figure 5:
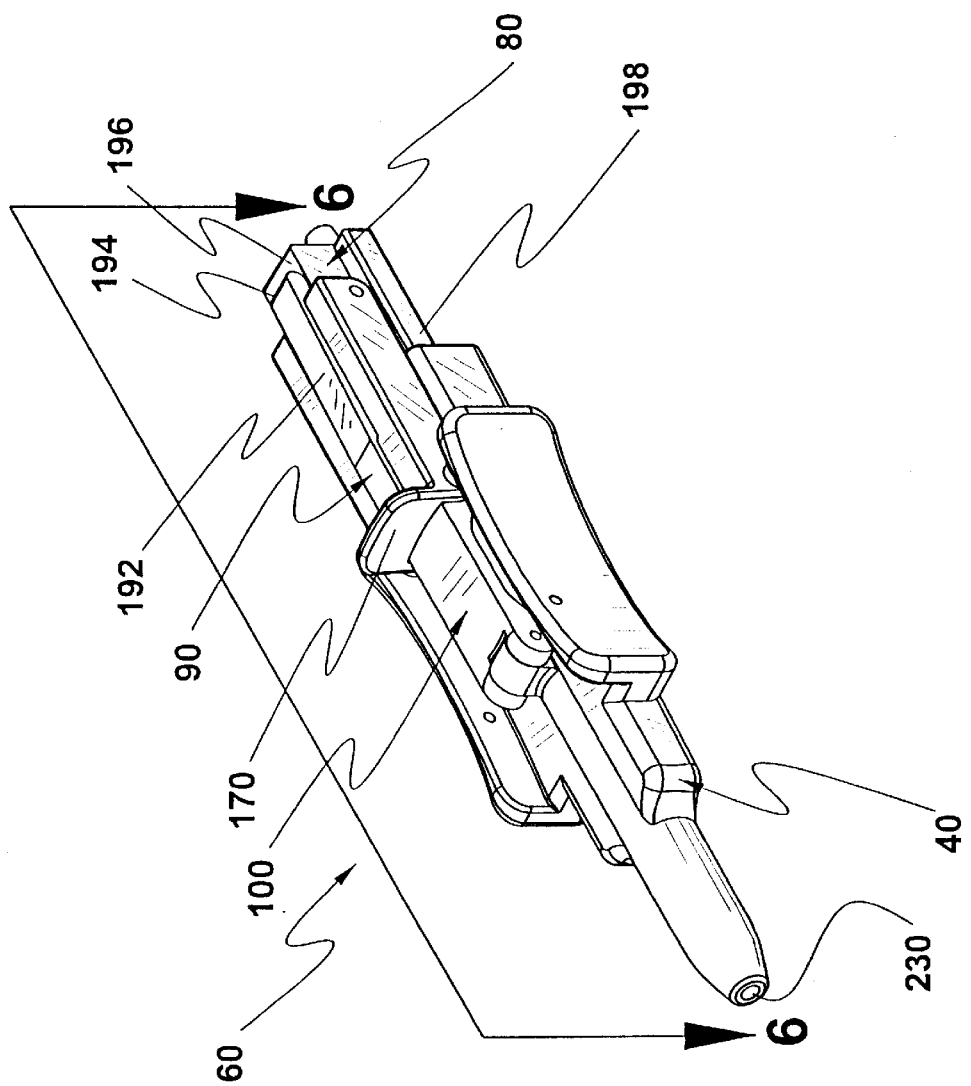
FIG. 5 is a perspective of the embodiment seen in FIGS. 1, 2, 3 and 4 wherein the needle is fully retracted.
Figure 6:
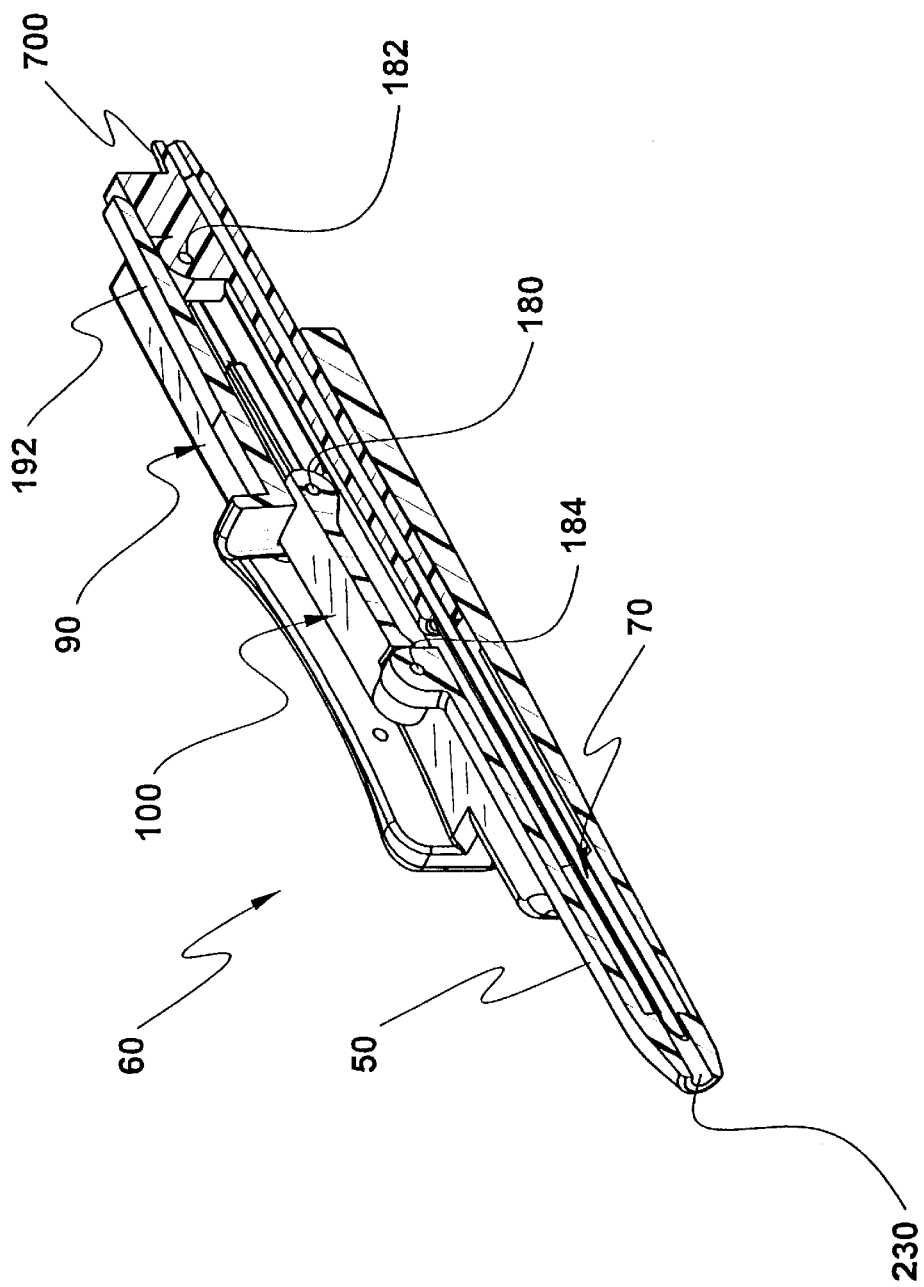
FIG. 6 is a cross section taken along lines 6—6 of the embodiment seen in FIG. 5 wherein the needle is also fully retracted.

Device 60 is seen in FIG. 5 to be at a state where needle 70 is fully retracted. Shaft 192 is returned to a non-stressed state. Arm 100 has pivoted about an angle of substantially 180° thereby displacing needle 70 approximately twice the length of arm 100. Also seen in FIG. 5 is one rail 198 of a pair of rails associated with needle hub assembly 30. The rails in cooperation with "U" shaped channel 110 restrain needle hub assembly 30 to slidable displacement in line with the long axis of needle 70. Safe containment of needle 70 within distal segment 50 is best seen in FIG. 6.

Figure 7:
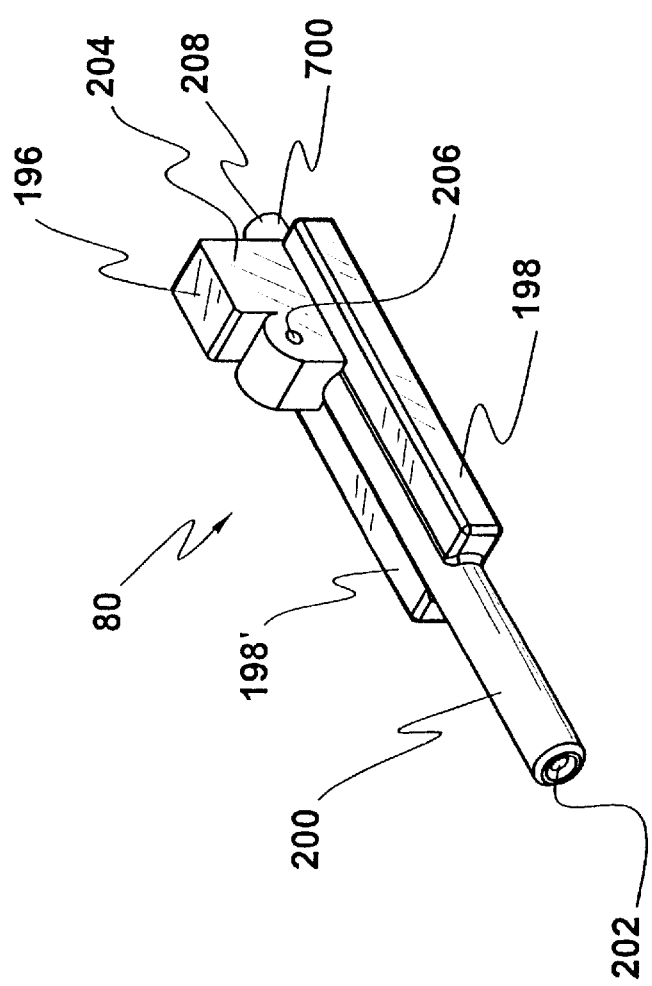
FIG. 7 is a needle hub portion of the device embodiment seen in FIG. 1.

Attention is now drawn to FIGS. 7–10 wherein needle hub 80, arm 100, arm 90 and body base part 122, respectively are seen as individual parts. Needle hub 80 is seen in FIG. 7 to comprise rail 198 and a juxtaposed rail 198'. Medially, hub 80 comprises an elongated hollow cylindrical part 200 wherein needle 70 is securely affixed within a distal orifice 202. At the proximal end needle hub 80 comprises pedestal 204, a superior surface of which forms top planar surface 196. A site 206 for hinge 182 is disposed near to, but distal from, pedestal 204. At the most proximal end, a fitting attachment 208 is disposed. Such fitting attachments are well known in the art of winged needle devices. While needle hub 80 may be made from a number of synthetic resinous materials, polyvinyl chloride is the current material of choice due to its strength, clarity and adhesive qualities.

Figure 8:
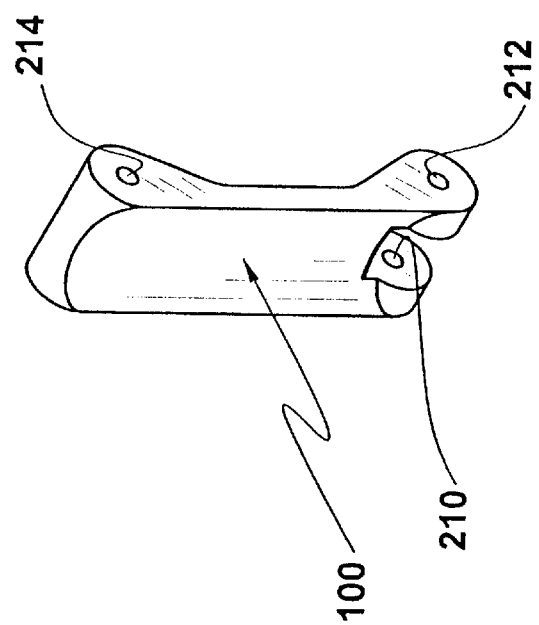
FIG. 8 is a perspective of a first articulating member of the device embodiment seen in FIG. 1.

Arm 100 is seen in FIG. 8. Arm 100 comprises sites 210 and 212 for hinge 184 and site 214 for hinge 180. The distance which separates sites 210 and 212 from 214 should be at least as long as one-half the length needle 70 extends from distal segment 50.

Two different perspective views of arm 90 are seen in FIGS. 9 and 9A. As earlier disclosed, arm 90 comprises an actuator tab 170 and a distortable shaft 192. In addition, arm 90 comprises sites 220 and 222 for hinge 182 and sites 224 and 226 for hinge 180. As the distance between sites 220/222 and 224/226 is greater than the distance which separates sites 210 and 212 from 214 (see FIG. 3), outward displacement of tab 170 greater than 90° is not required to cause arm 100 to pivot through a 180° arc. Note that shaft 192 is formed as a cut-out of a larger planar section 228 (see FIG. 9) of arm 90. The extended length of shaft 192 must be great enough to rest upon surface 196 of hub 80 when shaft 192 is unstressed and to remain in contact with pedestal 204 at all times while being stressed as needle 70 is retracted.

Figure 10:
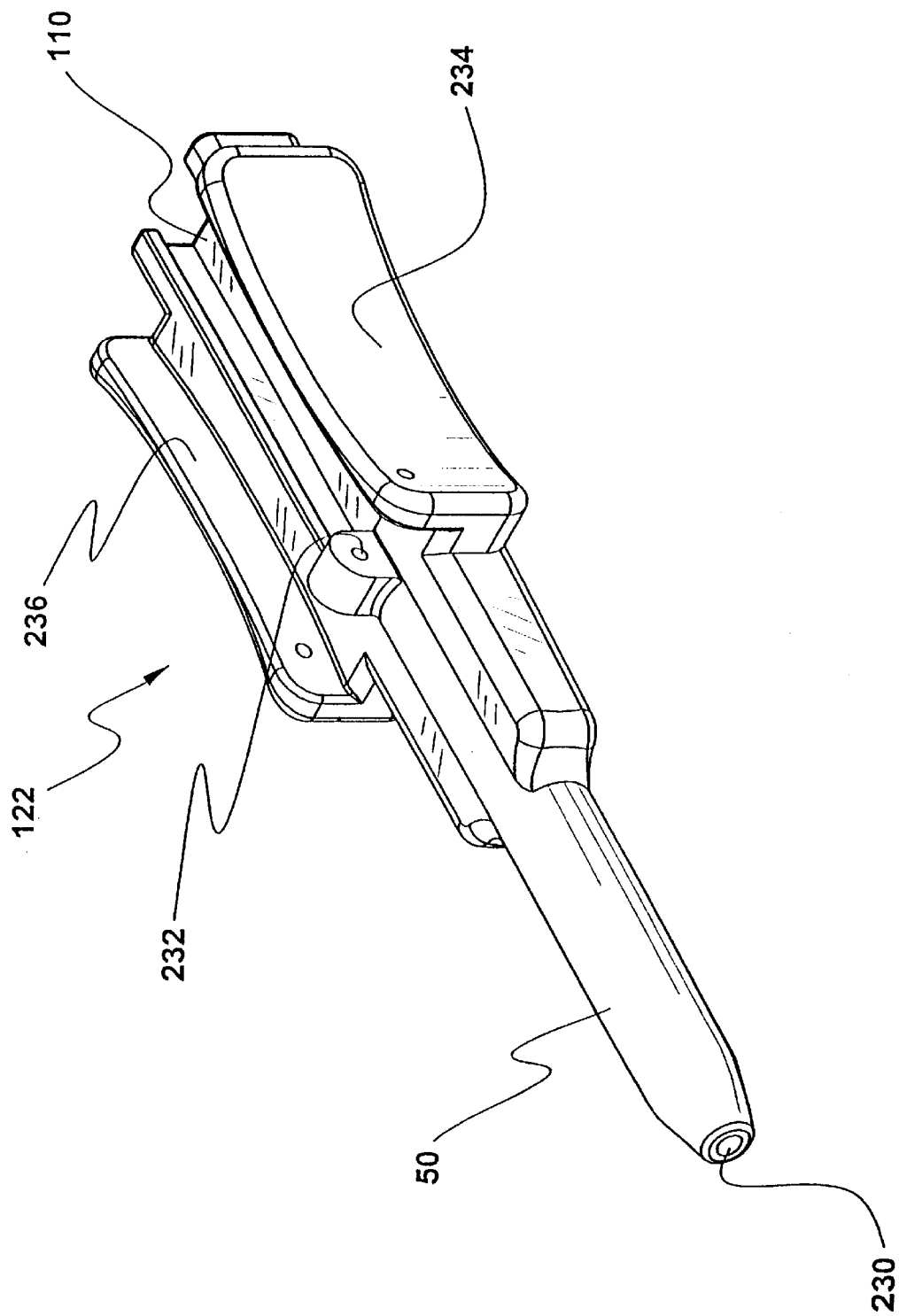
FIG. 10 is a perspective of a base portion of the device embodiment seen in FIG. 1.

Body base part 122 is seen in FIG. 10. As earlier disclosed, part 122 comprises distal segment 50 and "U" shaped channel 110. Part 122 also comprises a distal orifice 230 through which needle 70 is retracted, a site 232 for hinge 184 and a pair of juxtaposed handles 234 and 236 designed to meet the ergonomics of handling small needle percutaneous devices. Care should be taken to dispose handles 234 and 236 in a manner in which actuation of tab 170 is easy to accomplish with one digit of a hand (such as a forefinger) while holding the device with the thumb and middle finger of the same hand. Of course, other disposition of such handles is possible within the scope of the instant invention. In some cases, handles may not be used or provided.

Even though device 60 is stable in both the extended needle and retracted needle states, achievement of desired safety suggests at least a permanent latch/catch mechanism be employed to assure a retracted needle shall not escape from confinement of distal segment 50. While other latch/catch mechanisms may be employed within the scope of the instant invention, one example of such mechanisms is provided in FIGS. 11–13.

Figure 11:
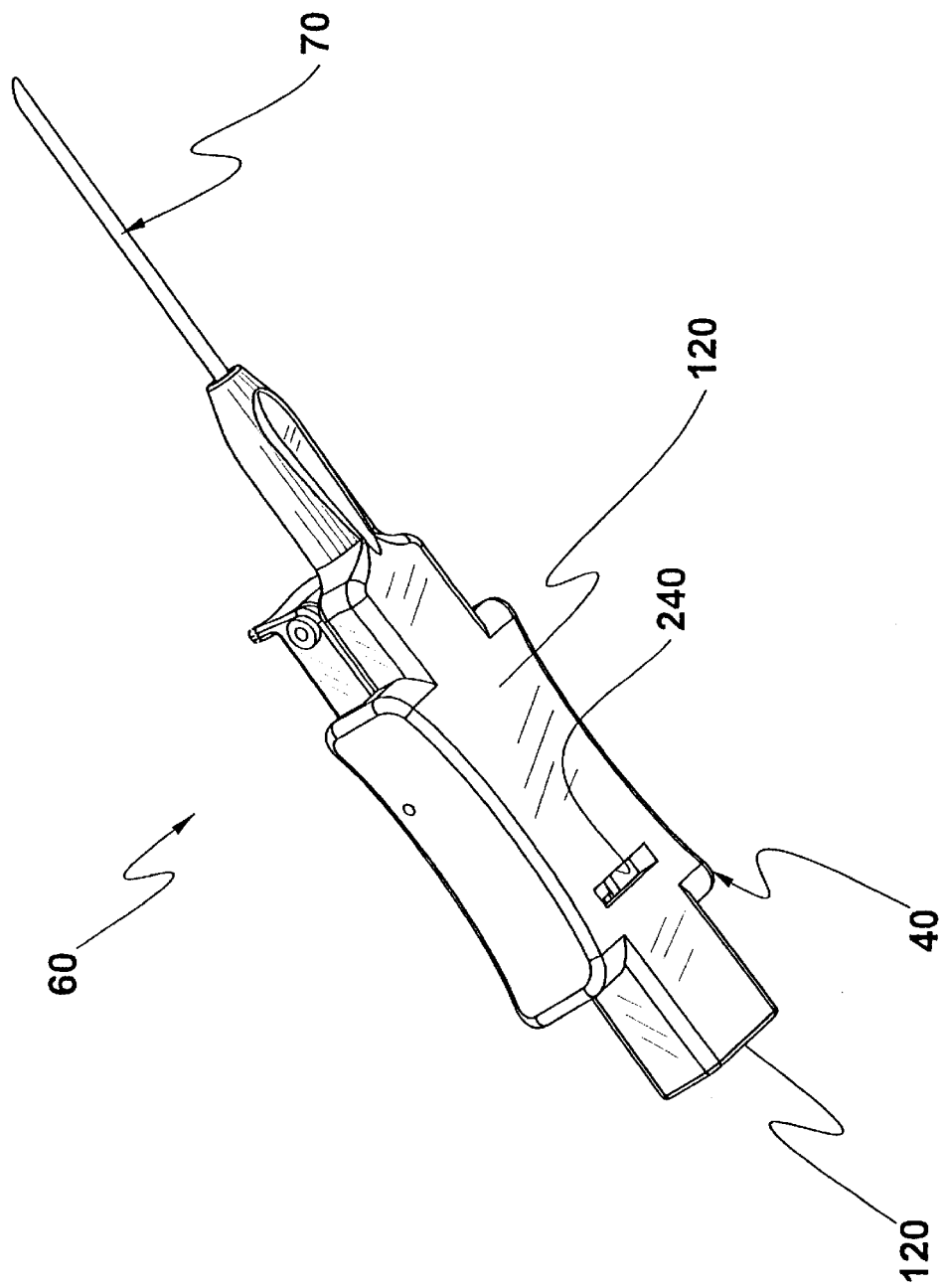
FIG. 11 is a perspective wherein the bottom of the base portion of FIG. 10 is clearly seen.

As seen in FIG. 11, a body assembly 40' of a device 60 comprises a slit 240, through base section 120, which is essentially transverse to the direction of needle 70 retraction to act as a catch for a part of a retracting needle hub. While slit 240 is seen to be a through hole through base section 120, a blind groove on the inward side of base section 120 would suffice for the catch and would be unaccessible from the exterior of body assembly 40'.

Figure 12:
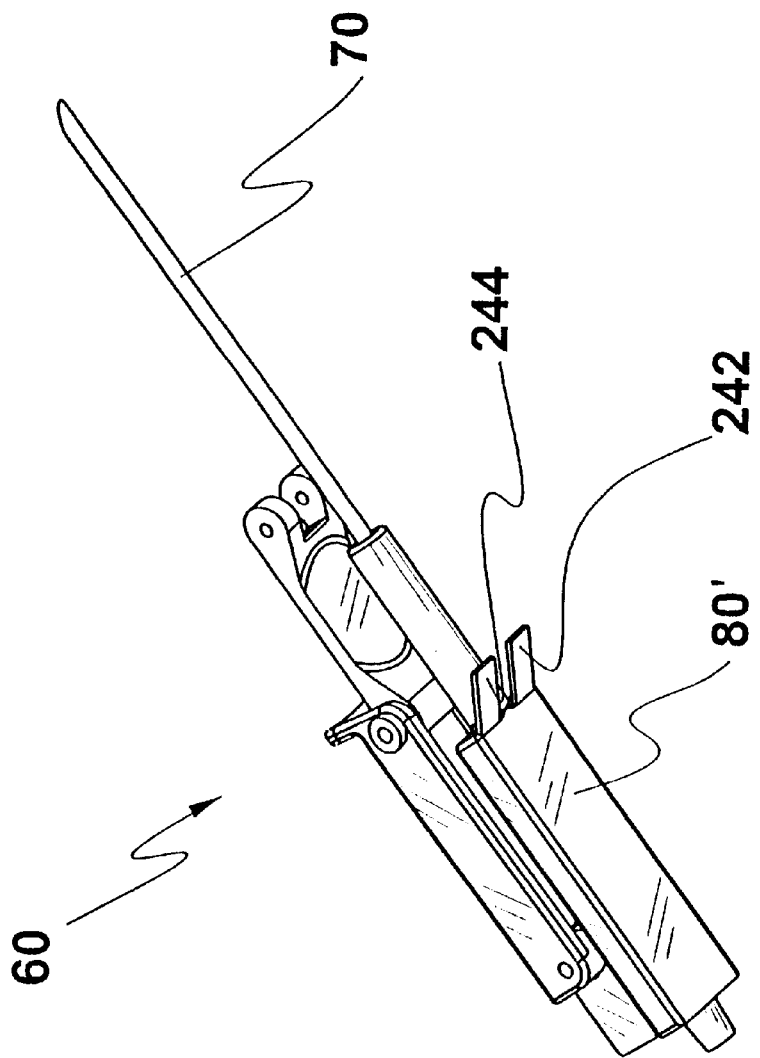
FIG. 12 is a perspective of the device embodiment seen in FIG. 1 with the base portion removed for visualizing locking tabs affixed to the needle hub portion.
Figure 13:
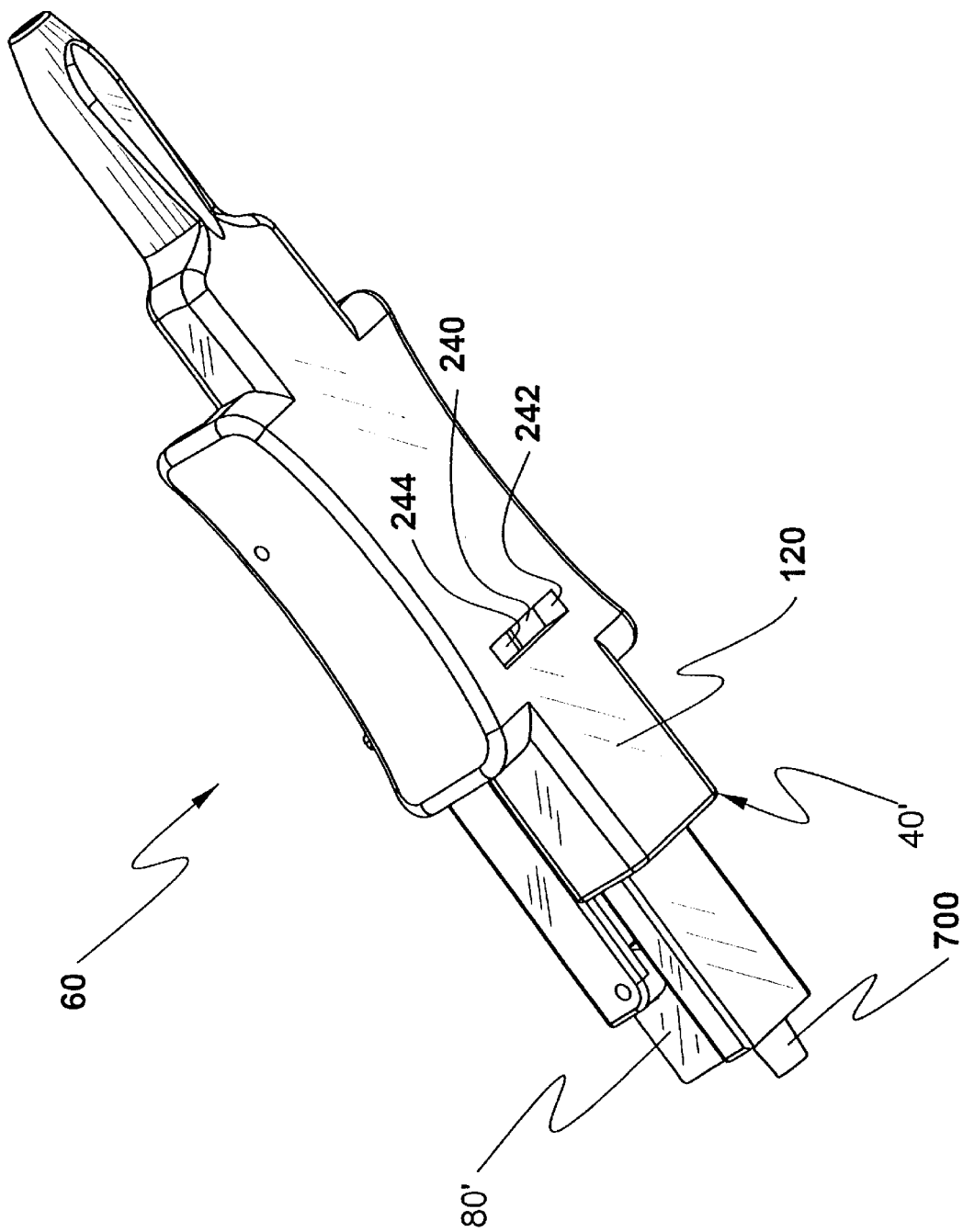
FIG. 13 is a perspective of the bottom of the device embodiment seen in 5 with the needle fully retracted.
Figure 14:
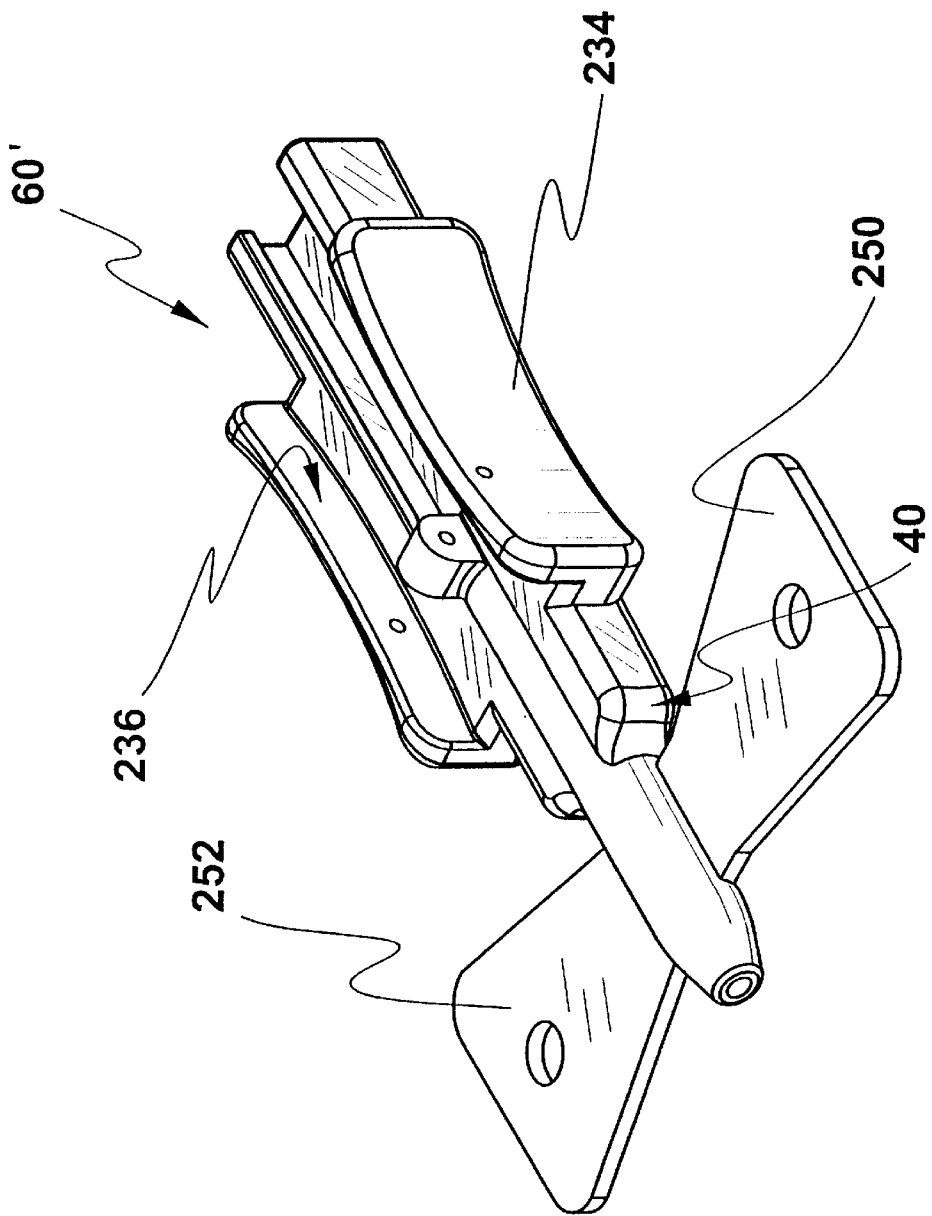
FIG. 14 is a perspective of a base portion similar to the base portion seen in FIG. 11 but having wings affixed thereto.

Parts have been removed from body assembly 40' to permit a hub 80' to be clearly seen in FIG. 12. Hub 80' comprises a pair of latch tabs 242 and 244 which are molded or otherwise biased downward toward base section 120 (not seen in FIG. 12) when disposed thereby. Depending upon hub material used, it may be advisable to provide grooves in base section 120 which provide relief for tabs 242 and 244 while needle 70 is disposed for use in a medical procedure. As seen in FIG. 13, full retraction of needle hub 80' permits tabs 242 and 244 to latch into the catch provided by slit 240, thereby precluding any extension of needle 70 out of body assembly 40'.

It is common in contemporary medical practice to use winged needle devices in procedures involving very small bore needles. While handles 234 and 236 will likely find application in many medical procedures, wings, such as wings 250 and 252 seen in FIG. 14, may be usefully added to body assembly 40, or 40', which is seen therein in part of device 60'. In such a case, handles 234 and 236 may be optionally removed.

Figure 15:
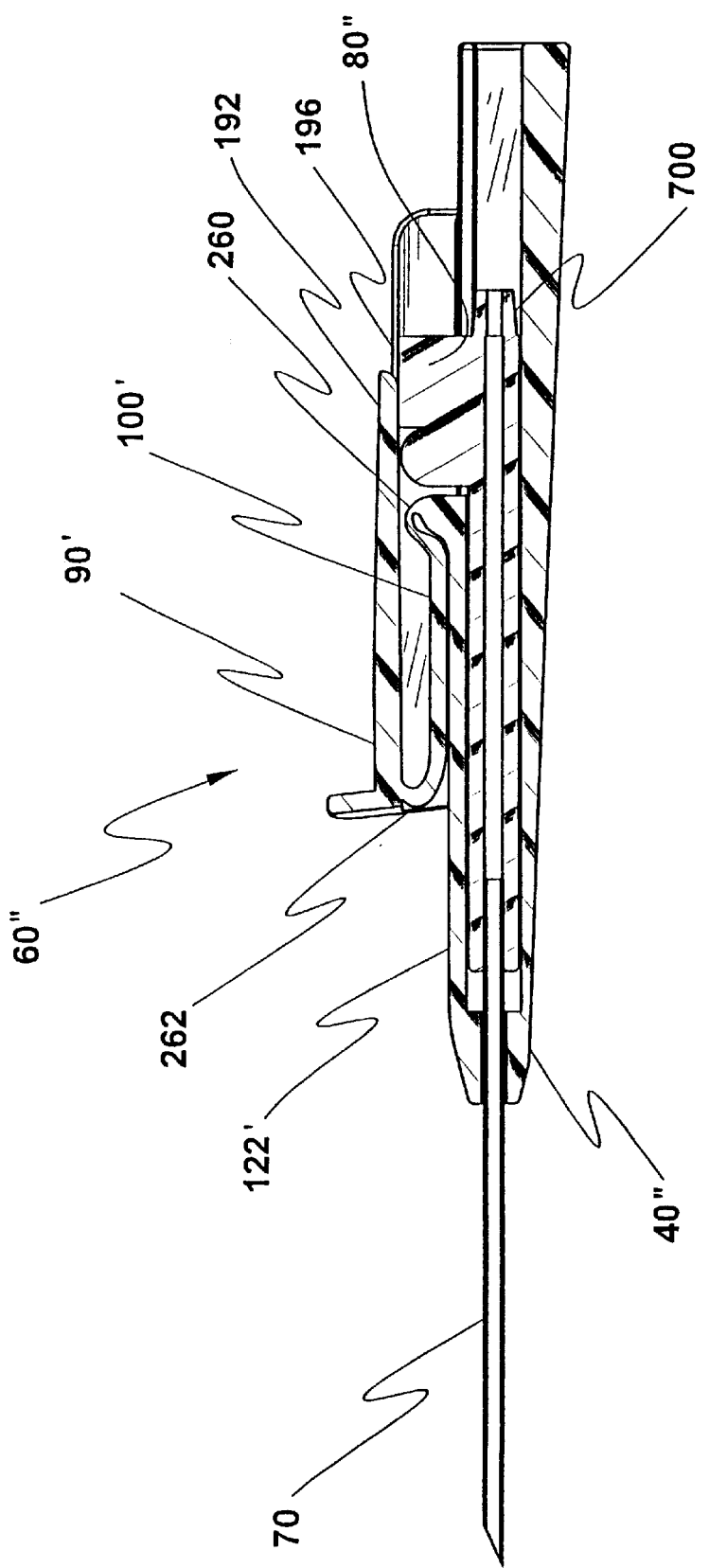
FIG. 15 is a cross section similar to the cross section seen in FIG. 3, but for another device embodiment of the invention wherein the base member and first and second articulating members are joined by living hinges preferably formed within a single injection mold.
Figure 16:
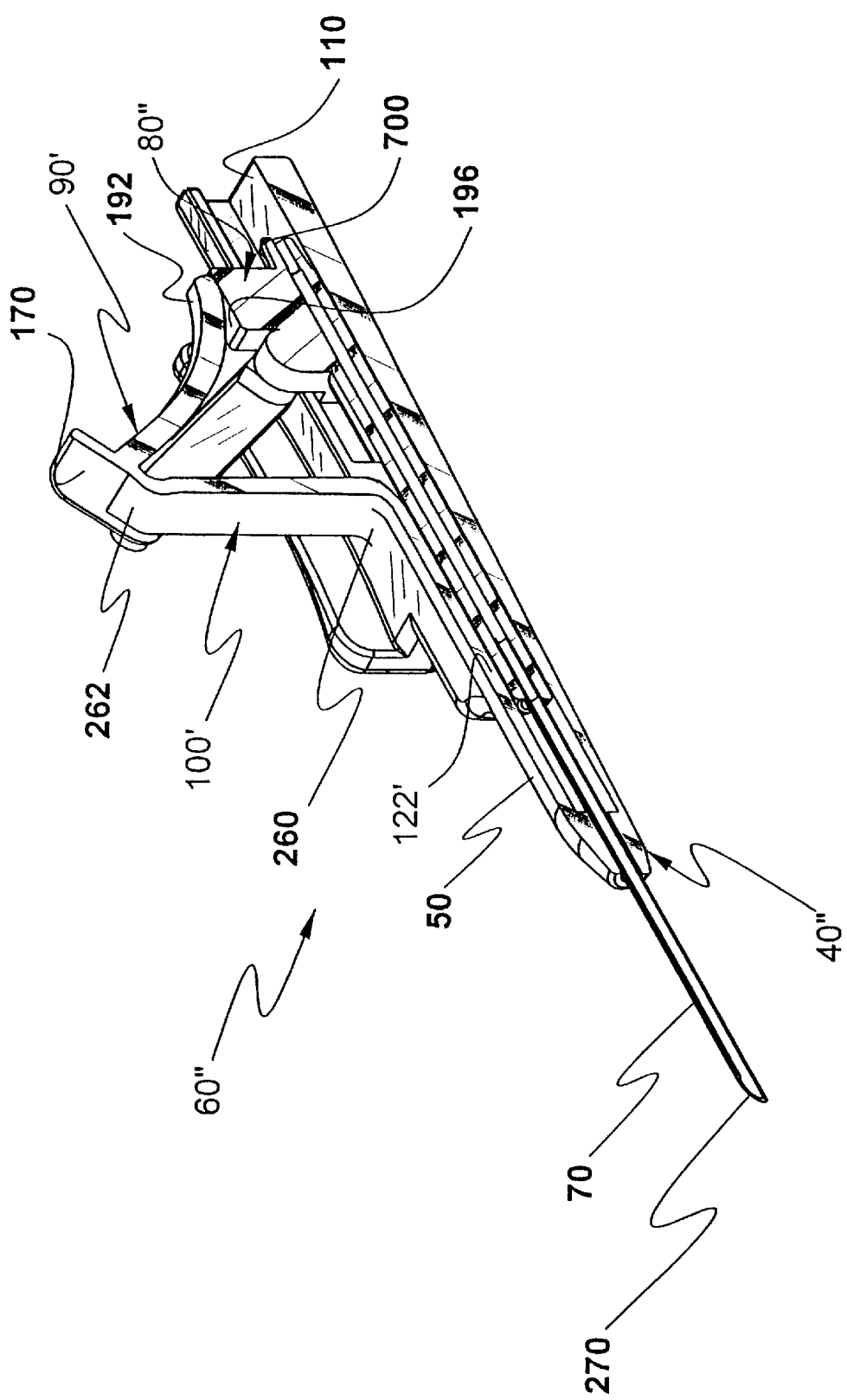
FIG. 16 is a cross section of a perspective, of the device embodiment seen in FIG. 15, wherein the needle is partially retracted.
Figure 17:
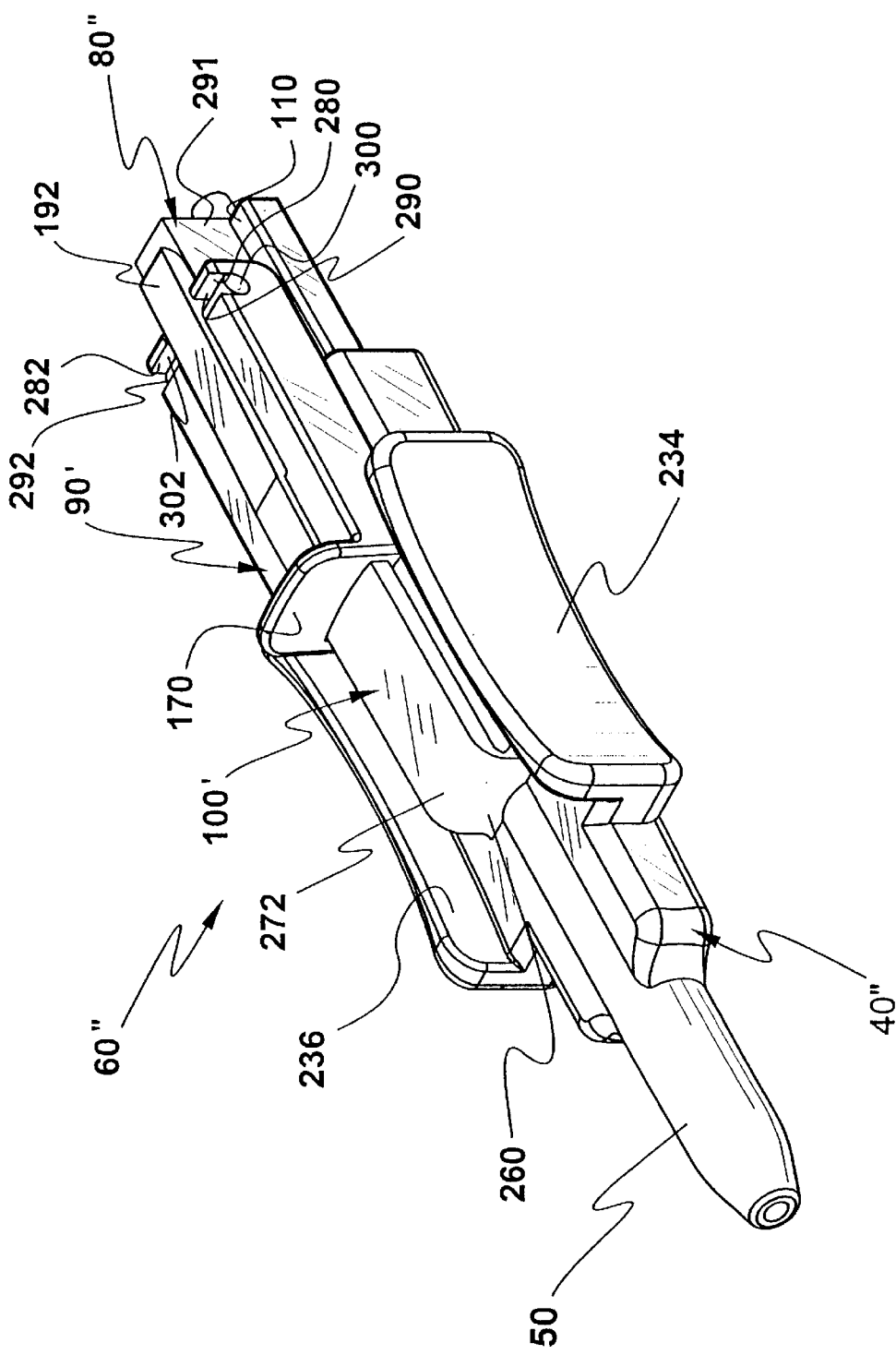
FIG. 17 is a perspective of the device embodiment, seen in FIGS. 15 and 16, wherein the needle is fully retracted.

While devices 60 and 60' may be effectively used in a medical procedure, costs of producing the multiple numbers of parts (e.g. body part 122, arms 90 and 100 and hinges 180, 182 and 184) and assembling those parts into a complete body assembly (similar in function to body assembly 40) would likely make device 10 commercially unviable. However, through injection molding and use of appropriate material having clarity to see a flash chamber, rigidity to retract and safely restrain needle hub assembly 30 and flexibility to form useful living hinges permits all of a part providing the function of body assembly 40 to be made as a single injection molded part. Such a part (numbered 40") is seen in FIGS. 15–17. Note that device 60" performs the same functions as devices 60 and 60', but is fabricated from but two injection molded parts, body assembly 40" and needle hub 80".

As seen in FIG. 15, body assembly 40" comprises a body part 122' (similar in form and function to body part 122) hingeably interconnected to an arm 100' through a living hinge 260. In similar fashion, an arm 90' is interconnected to arm 100' through a living hinge 262. Arm 90' also comprises a snap hinge connection to a needle hub 80" which is disclosed in detail hereafter. When the needle 70 is disposed for use in a medical procedure as seen in FIG. 15, arm 90' is compactly, horizontally folded in superior disposition relative to arm 100' which is also horizontally disposed to assure a compactness of device 60".

To retract needle 70 and its sharpened tip 270 into the safety of distal segment 50, tab 170 is pivoted proximally away from close juxtaposition with arm 100' as seen in FIG. 16. Note that arm 90', like arm 90, comprises a shaft 192 which is disposed to rest against top surface 196, of hub 80". As tab 170 is proximally pivoted, a hinged connection (disclosed in detail hereafter) between arm 90' and hub 80" urges hub 80" (and therefore needle 70 and needle tip 270 proximally) along "U" shaped channel 110. Such articulation of tab 170 also causes shaft 192 to be stressed as the distance between tab 170 and surface 196 is decreased by articulation of arm 90'. This stressing increases until arm 100' is rotated to be perpendicular relative to body part 122'. Once the point of perpendicularity is passed and arm 100' forms an acute angle relative to body part 122', the stress in shaft 192 is progressively relieved, the subsequent release of energy stored in shaft 192 folds arm 90' and tab 170 into a compact relationship with body part 122'.

Thereat, needle 70 and needle tip 270 are fully retracted into distal segment 50 for safe containment. Full retraction may be accomplished by release of force stored within shaft 192 or further enabled by application of digital force against tab 170 or alternatively against a superior revealed surface 272 (see FIG. 17) of pivoted arm 100' to reduce travel distance required of the activating digit to approximately one-half the length of needle 70. For facile operation, handles 234 and 236 may be displaced proximally and distally as ergonomic factors dictate.

Figure 18:
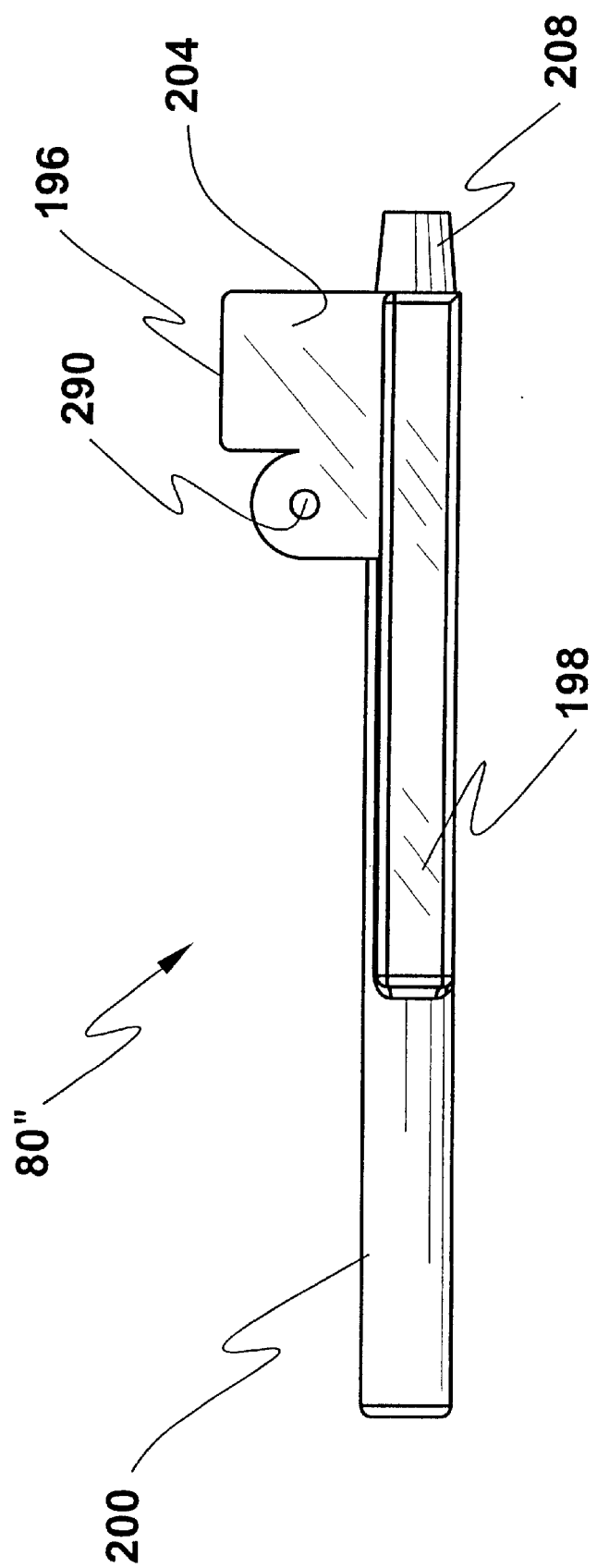
FIG. 18 is a side elevation of a hub part of the device embodiment seen in FIGS. 16, 17 and 18.
Figure 19:
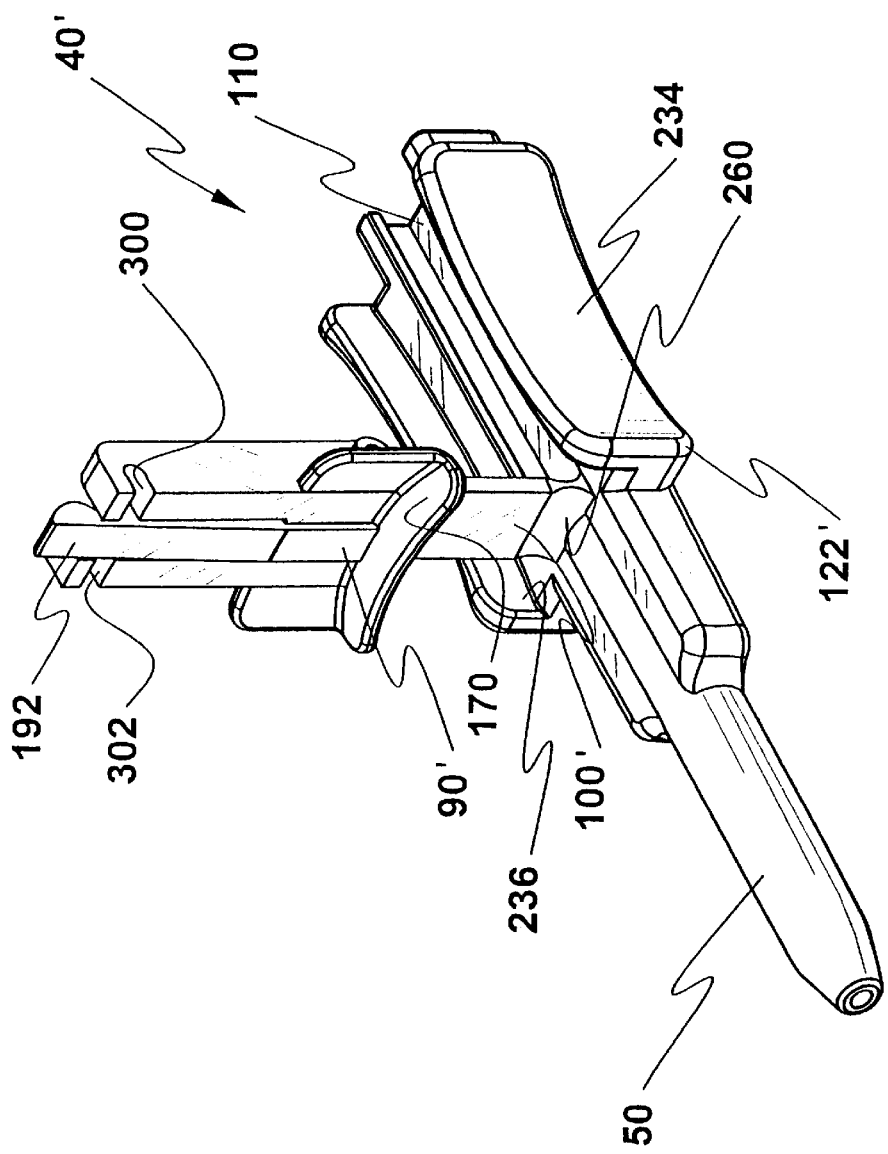
FIG. 19 is a perspective of a single molded part which may be used in the device embodiment seen in FIG. 15, the part comprising a base member and first and second articulating members.

Hinge connections 280 and 282 between arm 90' and hub 80" are seen in various parts and states in FIGS. 17–19. For example in FIG. 17, hinge connection 280 is seen to comprise a cylindrical post 290 affixed on a lateral side 291 of hub 80" which is sized and disposed to be snugly contained in a circular slot 300. Similarly, hinge connection 282 comprises a cylindrical post 292 and a circular slot 302, juxtaposed on an opposite side of hub 80". Note that "U" shaped channel 110 in combination with hinge connections 280 and 282 securely maintain hub 80" for slidable displacement within channel 110. Disposition of post 290 on hub 80" is better seen in FIG. 18.

An example of body assembly 40" in an as molded state is seen in FIG. 19. Arms 90' and 100' are molded essentially in-line, orthogonal to body part 122'. In this manner, circular slots 300 and 302 are open to a horizontal mold pull. Note that articulating arm 90' through a near 180° arc and then, while holding arm 100' essentially vertical (orthogonal to body part 122'), inserting hub 80" into channel 100 until arm 90' "gives" to permit insertion of posts 290 and 292 into slots 300 and 302, respectively, securely affixes hub 80" to arm 90' within "U" shaped channel 110 throughout all positions in which hub 80" is displaced in needle extension and retraction. Body assembly 40" is preferably molded as a single part from polypropylene, although other synthetic resinous materials may be used within the scope of the invention.

Figure 20:
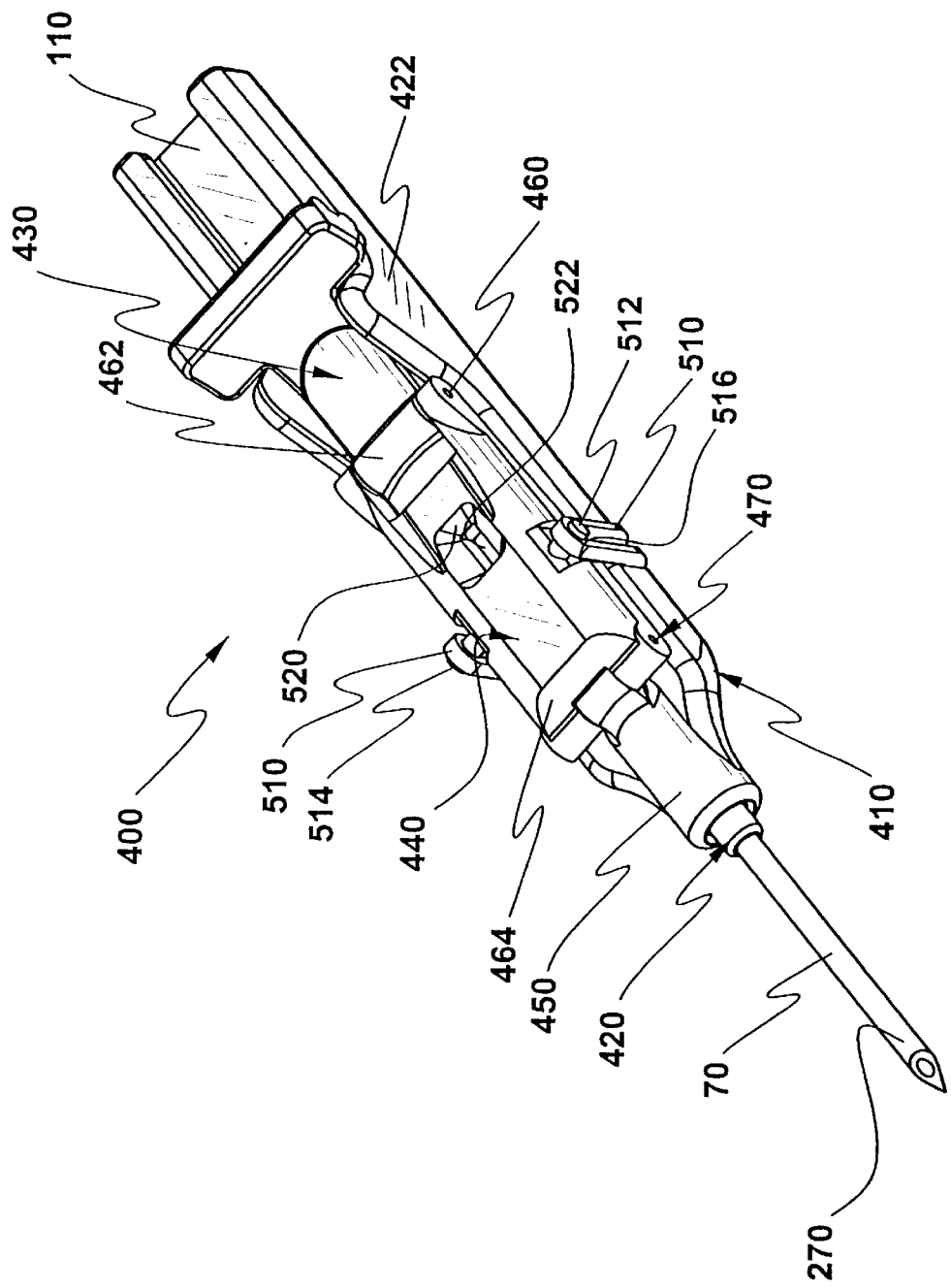
FIG. 20 is a perspective of yet another embodiment of the invention.
Figure 21:
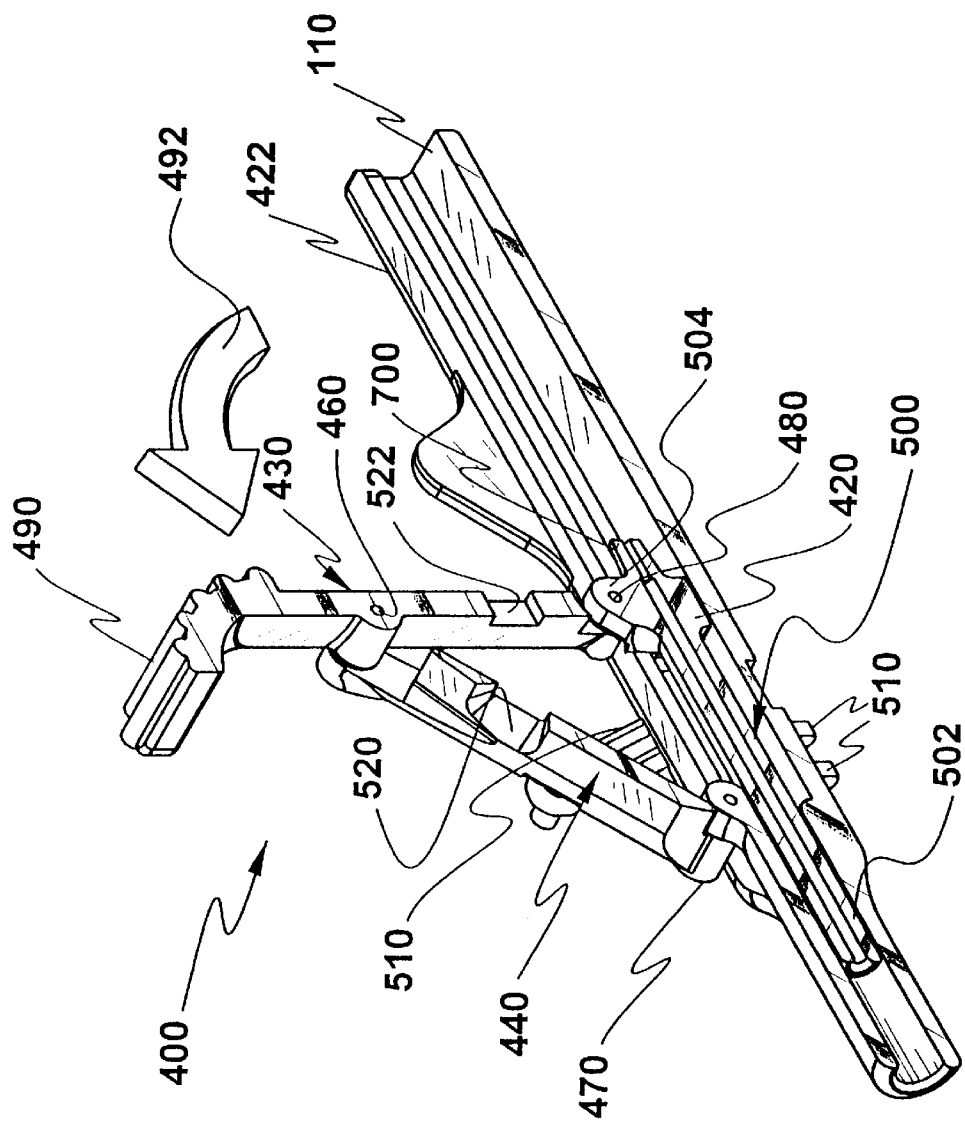
FIG. 21 is a lengthwise cross section of a perspective of the device embodiment, seen in FIG. 20, wherein the device is disposed in a mode wherein a needle (not seen in FIG. 21) affixed thereto would be partially retracted.
Figure 22:
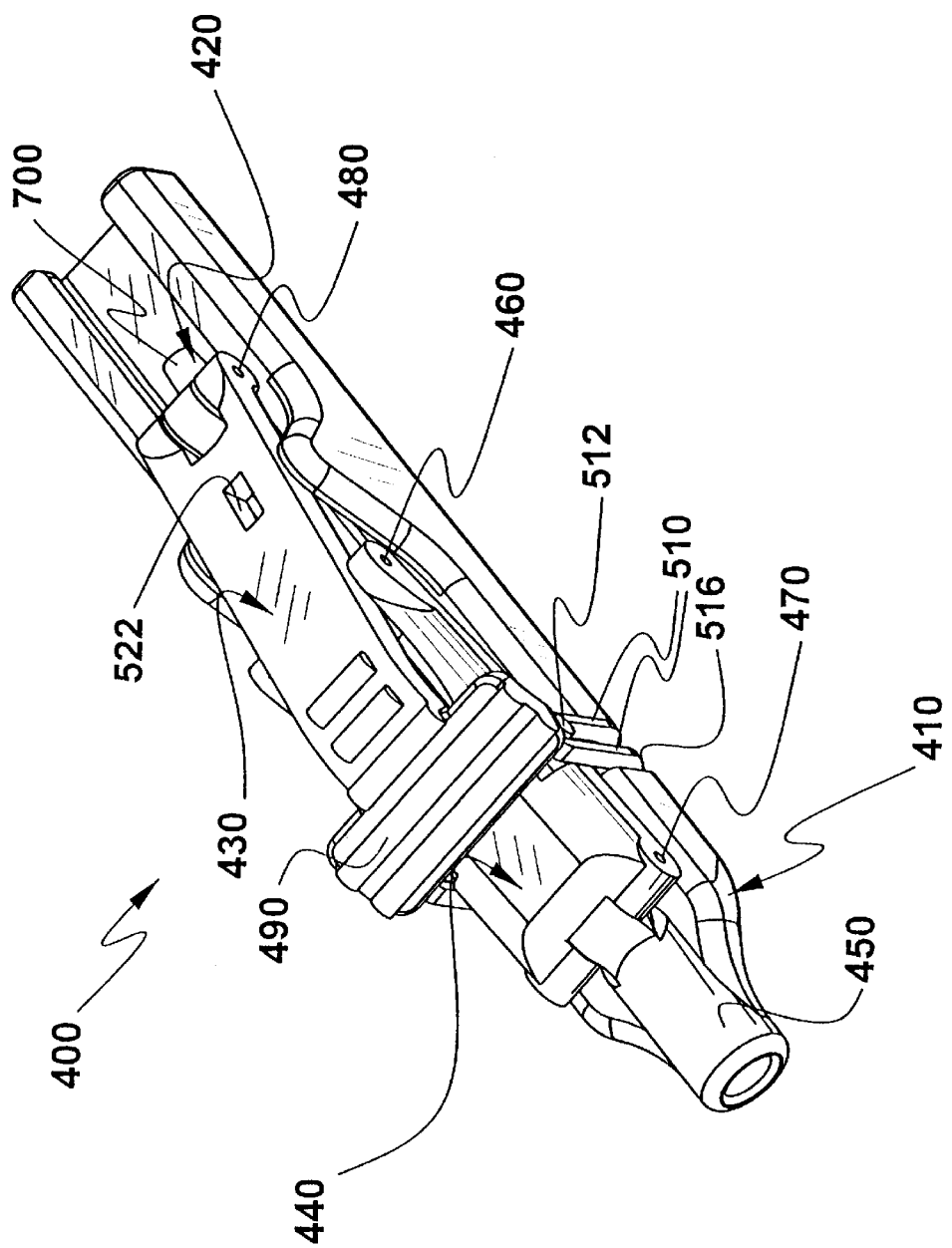
FIG. 22 is a perspective of the device embodiment, seen in FIG. 21, wherein the device is disposed in a mode wherein a needle affixed thereto would be fully retracted.
Figure 23:
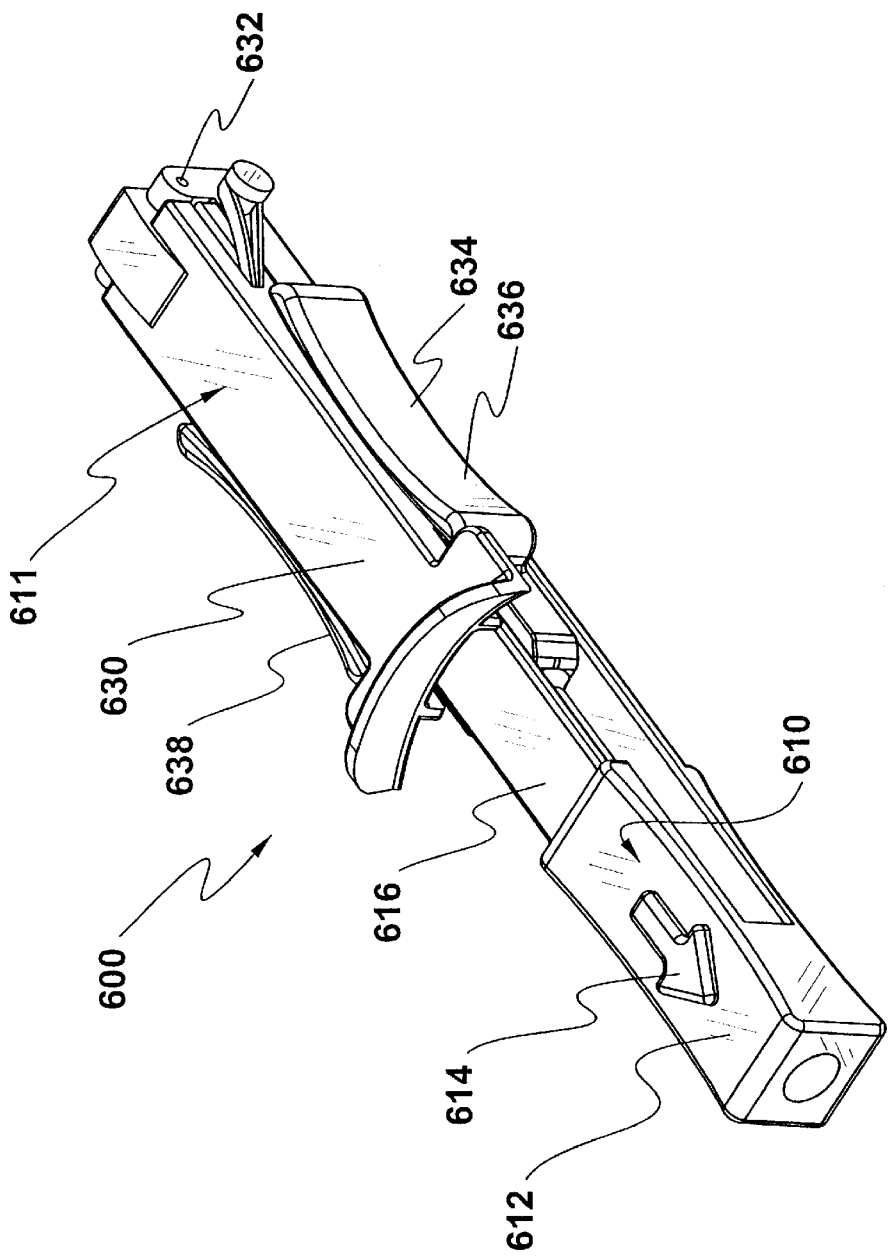
FIG. 23 is a perspective of an extendable/retractable embodiment of the invention.

As seen in FIGS. 20–22, device 400 represents another embodiment of the invention. Similar to the device embodiments 60 and 60', device 400 is an in-line, small bore needle safety retraction device. To permit more detail in presentation, the medical needle is removed in FIG. 21. Also no needle cover, such as cover 20, seen in FIG. 1, is shown in FIGS. 20–22, though such covers are commonly used to protect needle tips during transport and storage prior to use.

Referring to FIG. 20, device 400 is seen to comprise a body assembly 410 and a needle hub assembly 420, which is seen only in part after removal of the needle cover. Body assembly 410, similar to body assembly 40, comprises a base body part 422 and two arms, 430 and 440, which are pivoted to retract a medical needle 70 and its associated sharpened tip 270 into a safety enclosure afforded by a distal section 450 of body assembly 410. Similar to base body part 122 of body assembly 40, base body part 422 comprises a "U" shaped channel, which is also referenced by 110 and which provides slidable containment of needle hub assembly 420.

Arm 430 comprises a medially disposed hinge connection 460 to a proximal end 462 of arm 440. On a distal end 464, arm 440 further comprises a hinge connection 470 to base body part 422. As is clearly seen in FIG. 21, arm 430 comprises a hinge connection 480 which is initially distally disposed relative to hinge connection 460 while needle 70 is disposed for use in a medical procedure. Arm 430 also comprises a needle retraction actuation tab 490 which is proximally disposed while needle 70 is disposed for use in the medical procedure and which is displaced outwardly and distally away from base body part 422 in the direction of arrow 492 to cause needle 70 to retract into base body part 422.

Needle hub assembly 420 comprises a needle hub 500 and medical needle 70 with sharpened tip 270 (not seen in FIG. 21). Needle hub 500 comprises an elongated distal nose section 502 into which a proximal end of needle 70 is securely affixed and a proximal hinge connection part 504 by which arm 430 is hingeably affixed to hub 500 such that when arm 430 is pivoted about hinge 460, hub 500 and needle 70 are proximally displaced.

Needle hub assembly 420 is totally retracted into safety of confinement of needle 70 and needle tip 270 into distal section 450 by outward and then inward pivoted displacement of tab 490. The first position (for medical use) of arm 430 is seen in FIG. 20. A medially disposed pivoted arm 430 is seen in FIG. 21 and a completely rotated arm 430 is seen in FIG. 22. Attention is now drawn to FIG. 20 wherein an elastic band 510 is seen to be disposed about a pair of horizontally disposed pegs 512 and 514, transversely affixed to arm 440 and further about a channel 516 in base body part 422. Note that elastic band 510 is relatively unstressed while device 400 is disposed for use in the medical procedure. It is stretched to elastically store energy as arm 440 is displaced away from base part 422 as a result of tab 490 (and arm 430) being outwardly displaced. Then, as tab 490 is pivoted distally until arm 430 rotates to form an acute angle relative to base part 422, the energy stored in elastic band 510 urges arm 440 and therefore arm 430 to complete articulation and close upon base body part 422. Note that, in this case, arm 430 has proceeded from a position which was inferior to arm 440 to become disposed in a superior relation thereto. In this manner, device 400 provides a power assist to complete safety retraction of needle 70 and its sharpened tip 270 into distal section 450.

Attention is again drawn to FIG. 21 wherein a pair of in-line slots 520 and 522 are disposed in arms 440 and 430, respectively. These in-line slots provide a free optical pathway to visualize tubing affixed to needle hub needle hub assembly 420 for an early indication of blood flash as needle tip 270 enters a blood vessel.

Reference is now made to FIGS. 23–27 wherein a manual extension/powered needle retraction device 600 is seen. Device 600 comprises a protective needle extending cover 610 and a needle insertion and retraction implement 611.

It should be noted that pivoting actuator tabs 170 and arcuately outward provides a significant mechanical advantage when retraction is initiated. As each tab moves in an arc throughout needle retraction, beginning motion of each actuator is essentially orthogonal to direction of needle 70 travel such the needle 70 travel rate is small relative to actuator trave rate. Only at the apex of actuation (actuator is furthest outwardly displaced) is actuator travel rate equal to needle travel rate. Such mechanical advantage facilitates overcoming stiction in early needle and device actuation.

Figure 26:
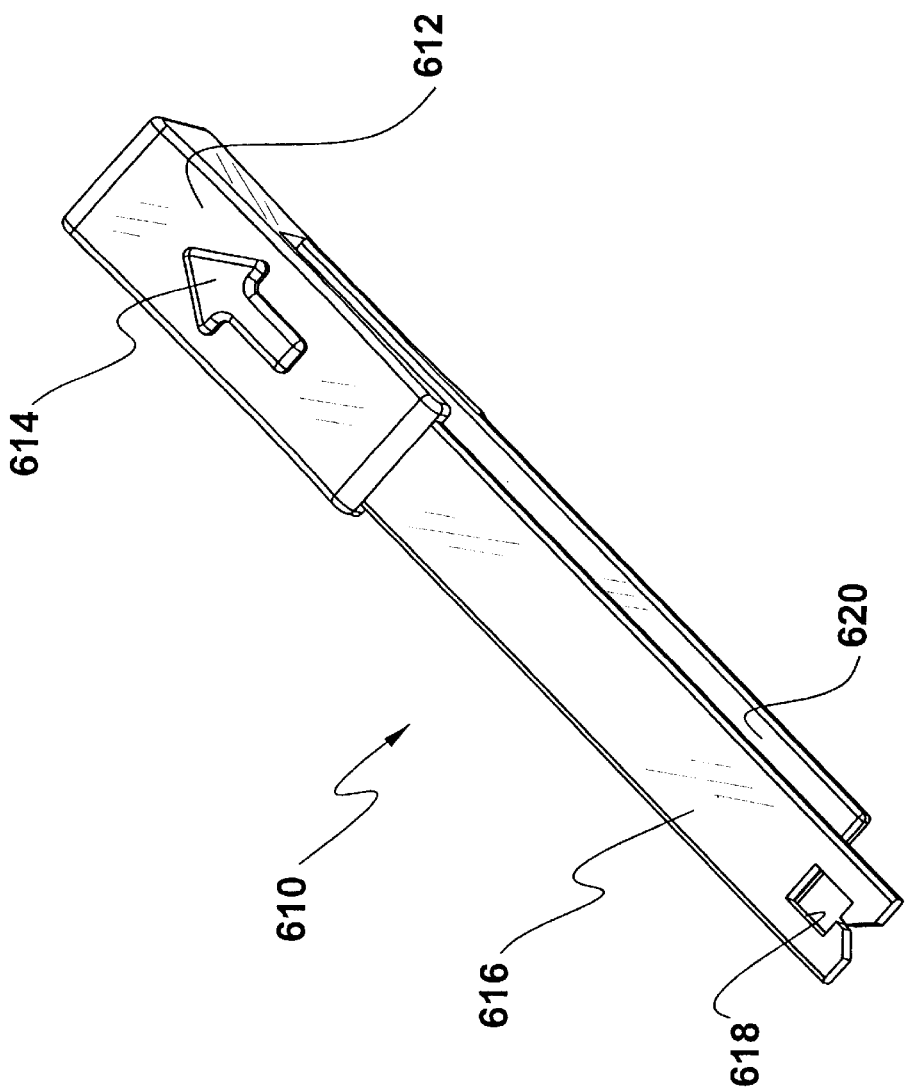
FIG. 26 is a perspective of a needle extender/cover of the embodiment seen in FIG. 23.
Figure 27:
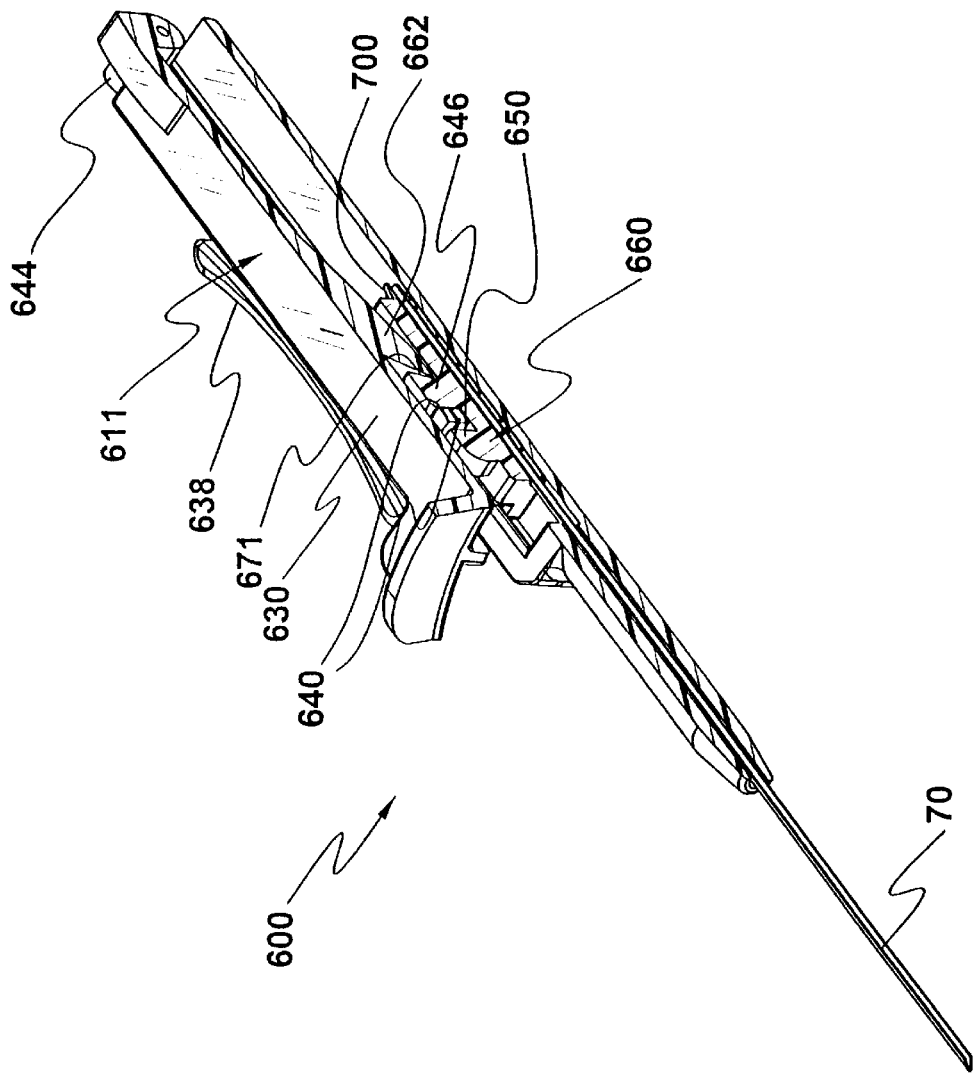
FIG. 27 is a lengthwise section similar to the section seen in FIG. 24 but with the cover seen in FIG. 26 removed and needle extended.

Needle extending cover 610 comprises an extender grip 612 which further comprises an optional arrow 614 which indicates direction of pull to extend a needle. Further, cover 610 comprises a first tine 616 which acts as a guide while pulling cover from implement 611 and further comprises a catch 618 which releasibly acts upon a latch (disclosed in detail hereafter) to extend the medical needle as cover is pulled from implement 611. As best seen in FIG. 26, a second tine 620, is inferiorly disposed to tine 616. Tine 620 acts as a guide to maintain catch 618 in contact with the latch until tine 620 is displaced from implement 611.

Referring again to FIG. 23, needle insertion and retraction implement 611 comprises a retraction actuator 630 connected through a hinge 632 to a base part 634. Implement 611 also comprises side handles 636 and 638 for facile handling.

Figure 25:
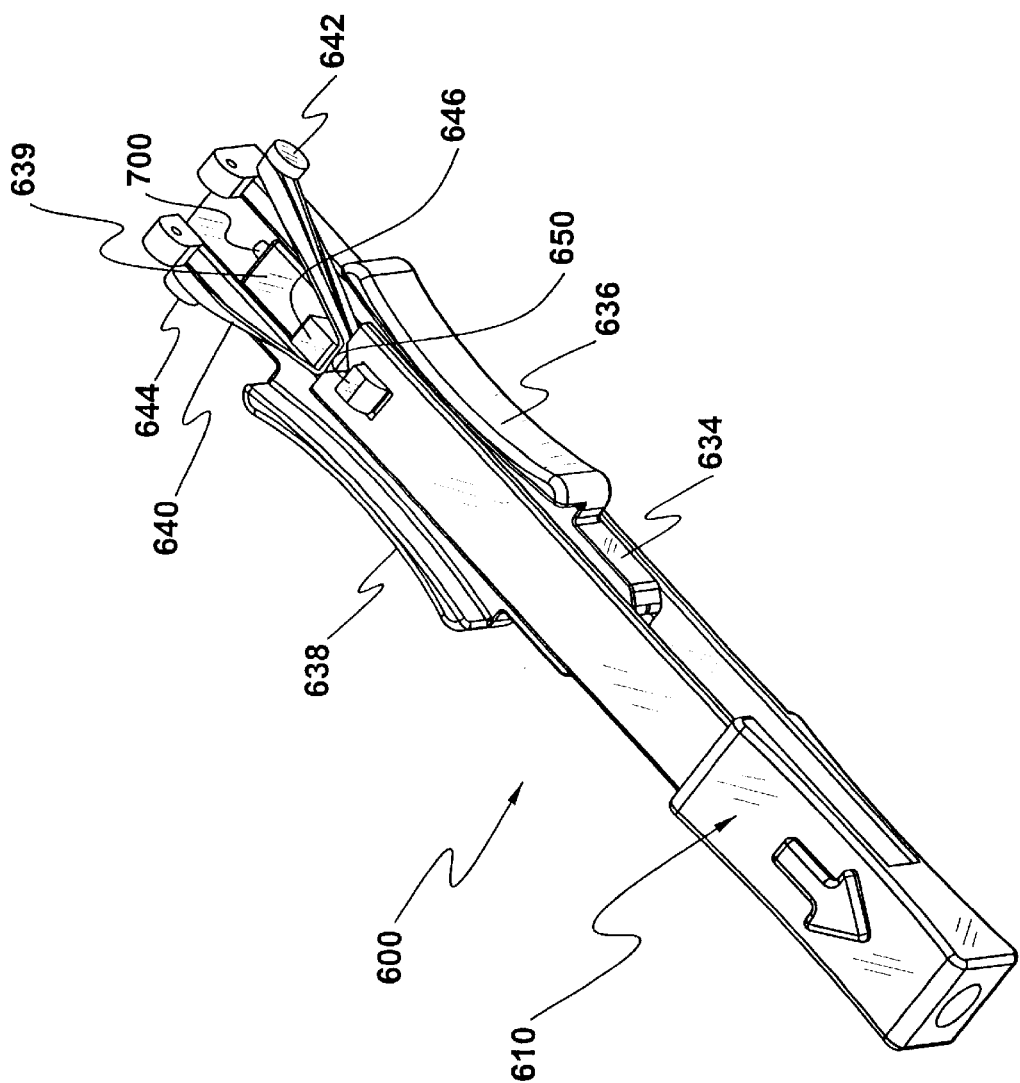
FIG. 25 is a perspective of the embodiment seen in FIG. 23 with parts removed for clarity of some internal parts.

In FIG. 25, actuator 630 is removed from hinge 632 to provide parts hidden thereunder to be seen. One part, which is fractionally seen is a needle hub assembly 639. Implement 611 further comprises an elastically distendable part such as a rubber band 640 disposed about a pair of laterally disposed posts 642 and 644 and a superiorly disposed spile 646 which cooperatively act to retractably affix needle hub assembly 639 to base part 634 through rubber band 640. Needle hub assembly further comprises a superiorly extending latch part 650 which acts in cooperation with catch 618 to stretch and thereby store energy in rubber band 640. Note that a spring or other part may used in which energy can be stored as needle hub assembly 639 is extended.

Figure 24:
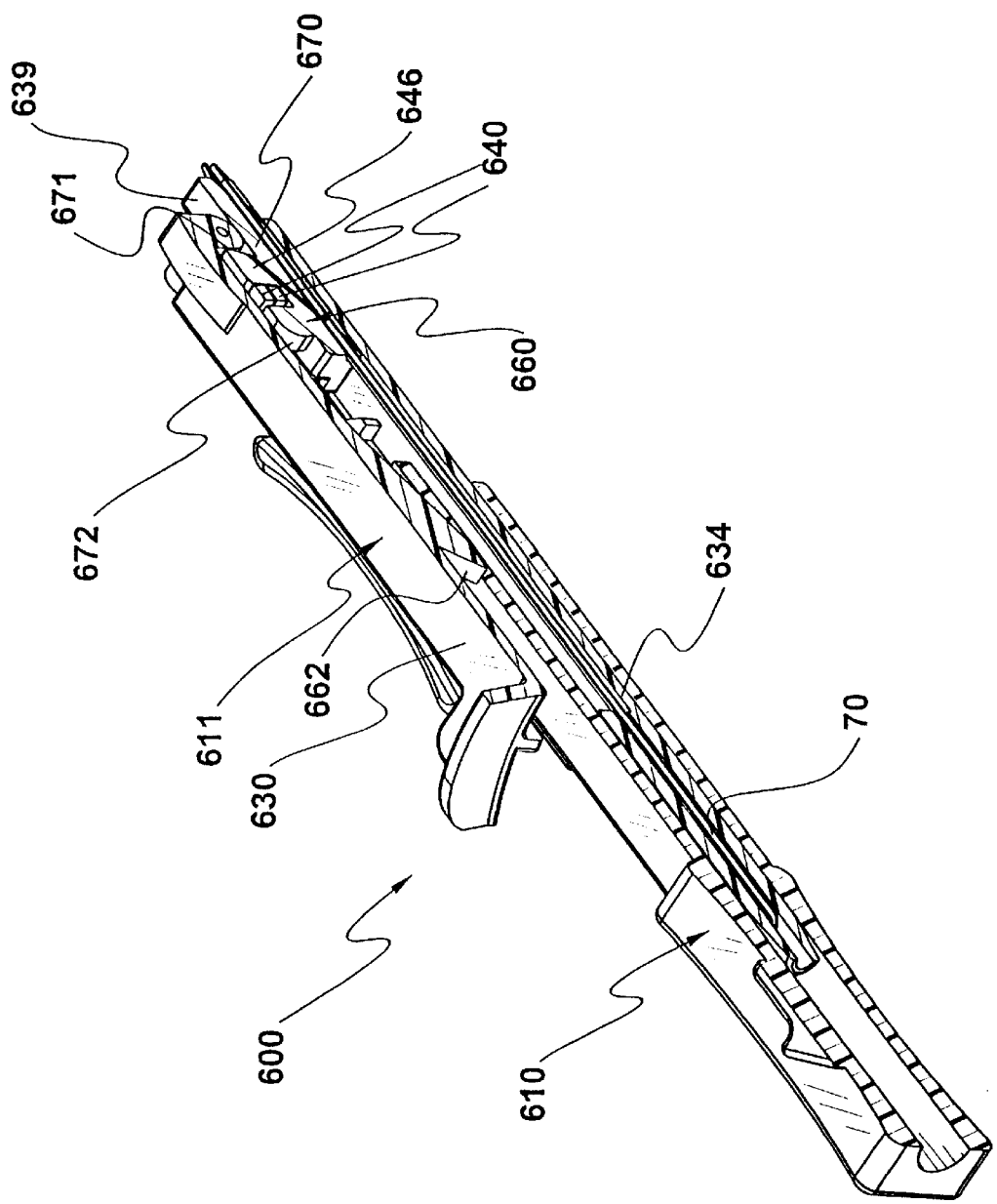
FIG. 24 is a lengthwise cross section of the embodiment seen in FIG. 23.

Reference is now made to FIG. 24 wherein implement 611 is seen to include a needle hub assembly 660 comprising a needle hub 670 securely affixed to a needle 70. In FIG. 24, cover 610 and, therefore, needle hub 670 and needle 70 are distally displaced, partially extending needle 70 from implement 611. Note that spile 646 extends superiorly from hub 670. A proximal face 671, of spile 646 comprises a catch. Also extending upward from hub 670 is a beveled part 672 used to facilitate travel of needle hub 670 as it is moved distally. Formed to operate in cooperative relationship with catch 671, is an inferiorly disposed latch part 662 subtending from actuator arm 630.

As a result of pulling and separating cover 610 from implement 611, latch 662 cooperatively engages catch 671 to secure needle assembly hub 660 in place for use in a medical procedure. At this point, rubber band 640 is stretched to maintain stability of needle 70. Needle hub assembly 660 is fully retracted to enclose needle 70 safely within base part 634 when actuator 630 is pivoted to release latch 662 from catch 671 by contraction of rubber band 640.

Each needle hub assembly, numbered 80, 80', 80", 500 and 660, comprises a proximal hub 700 which serves as a fitting attachment (see FIG. 7). Such attachments may be used to affix tubing or other medical connecting parts thereto, as is common in contemporary small bore needle devices. Also, generally, the needle hubs may be made from polyvinyl chloride. Each inter arm hinge (from the group of hinges numbered 180, 260 and 460) may be a living hinge formed as a molded part of so interconnected, associated arms. Each arm-to-base part hinge (from the group of hinges numbered 184, 470 and 632) may also be living hinges formed as a molded part of so interconnected arm and base parts. In this manner all base and arm parts for a particular device may be fabricated from a single injection molded part of a synthetic resinous material such as polypropylene.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety medical needle retracting device comprising:
   a needle hub assembly comprising a needle hub and a medical needle securely affixed at a proximal end thereof to a distal portion of the needle hub, said medical needle having a sharpened tip on a distal end and an elongated cannula disposed along a longitudinal axis of said hub assembly between the sharpened tip and the proximal end, said needle hub comprising a through hole in line with said cannula which provides a communicating fluid pathway there through;
   an elongated body assembly in which said needle hub assembly is slidably affixed, said elongated body assembly comprising a distal part, which is proximally disposed relative to said sharpened tip during a medical procedure and which surrounds and encloses said sharpened tip when the medical needle is retracted, and a proximal part which comprises a guide path through which a proximal portion of said needle hub is confined to glide proximally as said medical needle is retracted; and
   said elongated body assembly further comprising a pair of substantially rigid, elongated parts, a first end of one of the substantially rigid, elongated parts being hingeably affixed to a first end of the other substantially rigid, elongated part, a second end of the one of the pair of substantially rigid, elongated parts being hingeably affixed to said elongated body part and a second end of the other substantially rigid, elongated part being hingeably affixed to the needle hub such that the substantially rigid, elongated parts pivot in line with said longitudinal axis, with one of said parts rotating approximately 180° to urge retraction of said needle hub and medical needle from an extended state to a retracted state whereat said needle tip is enclosed within the distal part of the elongated body assembly.

2. A safety medical needle retracting device according to claim 1 further comprising a releasibly affixed needle cover which is removed to bare the needle for use in the medical procedure.

3. A safety medical needle retracting device according to claim 1 wherein one of said substantially rigid, elongated parts further comprises a distortable part which is stressed to store energy during a first portion of a needle retraction and which responsively releases the stored energy during a subsequent portion of needle retraction to assist completion of needle retraction.

4. A safety medical needle retraction device for use in percutaneous procedures, said device comprising:
- a needle enclosure housing assembly comprising:
  - a slender, elongated base part comprising an extended longitudinal axis and a planar slide channel for a needle hub assembly, said slide channel being disposed in-line with the longitudinal axis;
  - a first substantially rigid, elongated part;
  - a second substantially rigid, elongated part;
  - a first hinge connection adjoining one end of said first substantially rigid, elongated part to said second substantially rigid, elongated part such that rotation of the first substantially rigid, elongated part relative to the second substantially rigid, elongated part is in line with the longitudinal axis of the elongated base part;
  - a second hinge connection adjoining said base part to said first substantially rigid, elongated part at an end opposite the one end such that rotation of the first substantially rigid, elongated part is in line with the longitudinal axis of the base part;
- a needle hub assembly slidably disposed within said slide channel and comprising:
  - a medical needle comprising an elongated, hollow bore cannula defining a long axis of said needle hub assembly, said cannula having a sharpened tip disposed at a distal end and a proximally disposed end;
  - a needle hub comprising a through bore-hole disposed in alignment with said long axis and securely affixed at a distal end to said cannula and a proximally disposed hub whereat fluid flow apparatus is affixed for use in medical procedures;
- a third hinge connection disposed to hingeably affix said second substantially rigid, elongated part to said hub such that rotation of said second part is in line with the longitudinal axis of the base part;
- said substantially rigid, elongated parts and assemblies cooperating to fold into a first stable state such that the device has the characteristics of a compact, slender, low silhouette, medical implement when said medical needle is disposed for use in a medical procedure, further cooperating to retract said needle hub assembly as said substantially rigid, elongated parts are rotated away from said elongated base part and, whereby one of the substantially rigid, elongated parts is rotated substantially 180° to cooperatively fold said substantially rigid, elongated parts and displace said needle hub assembly to a second, stable state, thereby slidably retracting said needle hub along said slide channel to fully enclose said sharpened tip within a distal portion of said needle enclosure housing assembly.

5. The safety medical needle retraction device according to claim 4 wherein said needle hub comprises a latch and said needle enclosure housing assembly comprises a catch disposed to securely affix said needle hub when fully retracted to unreleasibly enclose said needle tip.

6. The safety medical needle retraction device according to claim 4 wherein said first and second hinges are living hinges formed as part of a single injection molded part comprising said substantially rigid, elongated parts and said needle enclosure housing assembly.

7. The safety medical needle retraction device according to claim 4 further comprising a needle cover which is disposed to shield said needle tip during shipment and storage and removed for access to said needle during a medical procedure.

8. The safety medical needle retraction device according to claim 4 wherein said elongated base part comprises a pair of wings such that the device may be used as a winged needle device.

9. The safety medical needle retraction device according to claim 4 wherein said elongated base part and needle hub assembly cooperatively each comprise a blood flash visualization section disposed proximally from said proximally disposed end of said cannula.

10. The safety medical needle retraction device according to claim 4 wherein said elongated base part comprises a pair of laterally juxtaposed handles.

11. The safety medical needle retraction device according to claim 4 wherein said slide channel comprises a "U" shaped channel formed from a planar base and adjoining vertical side walls having inwardly biased lips at the top thereof.

12. The safety medical needle retraction device according to claim 4 wherein the second substantially rigid, elongated part comprises means for rotating said substantially rigid, elongated part 180° to fully retract and enclose said needle tip.

13. The safety medical needle retraction device according to claim 4 wherein the first substantially rigid, elongated part comprises means for rotating said substantially rigid, elongated part 180° to fully retract and enclose said needle tip.

14. The safety medical needle retraction device according to claim 4 wherein said second substantially rigid, elongated part comprises an actuator tab disposed on a proximal end thereof.

15. The safety medical needle retraction device according to claim 4 wherein said second substantially rigid, elongated part comprises an actuator tab disposed on a distal end thereof.

16. The safety medical needle retraction device according to claim 4 wherein said second substantially rigid, elongated part comprises an elastic member which stores energy as the second substantially rigid, elongated part is outwardly displaced to initiate needle retraction and releases energy to urge the needle and needle tip into fully shielded enclosure as the second substantially rigid, elongated part is inwardly displaced.

17. The safety medical needle retraction device according to claim 4 wherein said needle enclosure housing assembly comprises an elastic band disposed between said elongated base part and the first substantially rigid, elongated part which stores energy as the first substantially rigid, elongated part is outwardly displaced to initiate needle retraction and releases energy to urge the needle and needle tip into fully shielded enclosure as the first substantially rigid, elongated part is inwardly displaced.

18. The safety medical needle retraction device according to claim 4 wherein said third hinge comprises means for snapping the corresponding hinged parts together.

19. A safety medical needle retracting device comprising:
- an elongated body assembly comprising a slide containment channel for a needle hub and a distal enclosure for safely enclosing a retracted medical needle;
- the needle hub being slidably disposed in said containment channel and securely affixed to the medical needle, the medical needle having a distally disposed sharpened tip for percutaneous entry and a long axis direction in line with said needle hub and said sharpened tip; and said body further comprising a needle retraction actuator which is a part of a communicating link between said hub and said body, said actuator being angularly displaced away from the rest of said device with a linear displacement along said long axis to urge the medical needle and the sharpened tip into said enclosure, the displacement of said actuator being a shorter distance than the travel distance of the sharpened tip.

20. An extendable and retractable, small cannula, safety medical needle device whereby a medical needle is retained within a housing for transport and storage, displaced to an extended state where the medical needle is exposed for a medical procedure and automatically retracted and enclosed at the end of the procedure, said device comprising:

a housing assembly comprising a base body part comprising a needle slide guide, an elastic member which stores energy as the medical needle is extended and an actuator which is displaced relative to the rest of the housing assembly to cause the needle to be automatically retracted, the actuator comprising a catch which cooperates with a latch on a needle hub to securely, but releasibly retain the medical needle in the extended state;

a needle hub assembly comprising the medical needle, the needle hub into which the medical needle is securely affixed, said needle hub comprising a bore-hole which provides a fluid path there through, the latch for said catch and a coupler which affixes the elastic member to the needle hub such that energy is stored in the elastic member as the medical needle is extended and is released to automatically retract the hub and associated needle when the actuator is displaced; and a needle cover which comprises a releasible puller which pulls the needle hub assembly outward to displace the needle to the extended state and then pulls free for ready disposal and immediate use of the device in a medical procedure.

21. A method for retracting a medical needle into safe confinement comprising the steps of:

providing a safety medical needle retracting device comprising:

a needle hub assembly comprising a needle hub and a medical needle securely affixed at a proximal end thereof to a distal portion of the needle hub, said medical needle having a sharpened tip on a distal end and an elongated cannula disposed along a longitudinal axis of said needle hub assembly between the sharpened tip and the proximal end, said needle hub comprising a through hole in line with said cannula for providing a communicating fluid pathway there through;

an elongated body assembly in which said needle hub assembly is slidably affixed, said elongated body assembly comprising a distal part, which is proximally disposed relative to said sharpened tip during a medical procedure and which surrounds and encloses said sharpened tip when the needle is retracted, a proximal part, which comprises a guide path through which a proximal portion of said needle hub is confined to glide proximally as said needle is retracted, and a pair of substantially rigid, elongated parts, a first end of one of the substantially rigid, elongated parts being hingeably affixed to a first end of the other substantially rigid, elongated part, a second end of the one of the pair of of the substantially rigid, elongated parts being hingeably affixed to said elongated body part and the second end of the other substantially rigid, elongated part being hingeably affixed to the needle hub such that, in combination, the substantially rigid, elongated parts pivot in line with said longitudinal axis, with one of said substantially rigid, elongated parts rotating approximately 180° to urge retraction of said needle hub and medical needle from an extended state to a retracted state whereat said needle tip is enclosed within the distal part;

initiating needle retraction through a mechanical advantage derived from outwardly pivoting said pivotal parts; and rotating one of said pivotal parts substantially 180° to completely retract and enclose the needle.

22. The method according to claim 21 wherein the rotating step comprises rotating the one of said pivotal parts distally.

23. The method according to claim 21 wherein the rotating step comprises rotating the one of said pivotal parts proximally.

* * * * *